US012727894B2

(12) United States Patent
Oluwasakin

(10) Patent No.: US 12,727,894 B2
(45) Date of Patent: Sep. 8, 2026

(54) DYNAMIC REFERENCE BASE FOR ROBOTIC-ASSISTED TOTAL HIP ARTHROPLASTY

(71) Applicant: GLOBUS MEDICAL, INC., Audubon, PA (US)

(72) Inventor: Israel Oluwasakin, Dresher, PA (US)

(73) Assignee: Globus Medical Inc., Audubon, PA (US)

( * ) Notice: Subject to any disclaimer, the term of this patent is extended or adjusted under 35 U.S.C. 154(b) by 95 days.

(21) Appl. No.: 18/770,993

(22) Filed: Jul. 12, 2024

(65) Prior Publication Data

US 2026/0013881 A1 Jan. 15, 2026

(51) Int. Cl.
*A61B 17/17* (2006.01)
*A61B 34/30* (2016.01)
*A61B 90/00* (2016.01)

(52) U.S. Cl.
CPC .......... *A61B 17/1742* (2013.01); *A61B 34/30* (2016.02); *A61B 90/39* (2016.02); *A61B 2090/3937* (2016.02); *A61B 2090/3983* (2016.02)

(58) Field of Classification Search
CPC ........................ A61B 2090/3983; A61B 90/39
See application file for complete search history.

(56) References Cited

U.S. PATENT DOCUMENTS 4,150,293 A 4/1979 Franke
5,246,010 A 9/1993 Gazzara et al.
5,354,314 A 10/1994 Hardy et al.
5,397,323 A 3/1995 Taylor et al.
5,598,453 A 1/1997 Baba et al.
5,772,594 A 6/1998 Barrick
5,791,908 A 8/1998 Gillio
5,820,559 A 10/1998 Ng et al.
5,825,982 A 10/1998 Wright et al.
5,887,121 A 3/1999 Funda et al.
5,911,449 A 6/1999 Daniele et al.
5,951,475 A 9/1999 Gueziec et al.
5,987,960 A 11/1999 Messner et al.
6,012,216 A 1/2000 Esteves et al.
6,031,888 A 2/2000 Ivan et al.
6,033,415 A 3/2000 Mittelstadt et al.
6,080,181 A 6/2000 Jensen et al.
6,106,511 A 8/2000 Jensen
6,122,541 A 9/2000 Cosman et al.
6,144,875 A 11/2000 Schweikard et al.
(Continued)

OTHER PUBLICATIONS

US 8,231,638 B2, 07/2012, Swarup et al. (withdrawn)

*Primary Examiner* — Andrew Yang

(57) ABSTRACT

A dynamic reference base (DRB) and associated method are provided for rigidly affixing an array frame to bone for use in navigated or robotic surgery. The DRB includes a bridge element that includes a connecting rod having a distal end and a proximal end; a clamp coupled to the distal end of the connecting rod; a first and a second pin guide extending distally from the clamp; a locking nut disposed on the clamp; and a clutch coupled to the proximal end of the connecting rod, the clutch being adapted to couple to the array frame. The DRB also includes the array frame, which is couplable to the clutch, and is adapted to include a plurality of tracking markers disposed thereon.

18 Claims, 20 Drawing Sheets

(56) References Cited

U.S. PATENT DOCUMENTS 6,157,853 A 12/2000 Blume et al.
6,167,145 A 12/2000 Foley et al.
6,167,292 A 12/2000 Badano et al.
6,201,984 B1 3/2001 Funda et al.
6,203,196 B1 3/2001 Meyer et al.
6,205,411 B1 3/2001 DiGioia, III et al.
6,212,419 B1 4/2001 Blume et al.
6,231,565 B1 5/2001 Tovey et al.
6,236,875 B1 5/2001 Bucholz et al.
6,246,900 B1 6/2001 Cosman et al.
6,301,495 B1 10/2001 Gueziec et al.
6,306,126 B1 10/2001 Montezuma
6,312,435 B1 11/2001 Wallace et al.
6,314,311 B1 11/2001 Williams et al.
6,320,929 B1 11/2001 Von Der Haar
6,322,567 B1 11/2001 Mittelstadt et al.
6,325,808 B1 12/2001 Bernard et al.
6,340,363 B1 1/2002 Bolger et al.
6,377,011 B1 4/2002 Ben-Ur
6,379,302 B1 4/2002 Kessman et al.
6,402,762 B2 6/2002 Hunter et al.
6,424,885 B1 7/2002 Niemeyer et al.
6,447,503 B1 9/2002 Wynne et al.
6,451,027 B1 9/2002 Cooper et al.
6,477,400 B1 11/2002 Barrick
6,484,049 B1 11/2002 Seeley et al.
6,487,267 B1 11/2002 Wolter
6,490,467 B1 12/2002 Bucholz et al.
6,490,475 B1 12/2002 Seeley et al.
6,499,488 B1 12/2002 Hunter et al.
6,501,981 B1 12/2002 Schweikard et al.
6,507,751 B2 1/2003 Blume et al.
6,535,756 B1 3/2003 Simon et al.
6,560,354 B1 5/2003 Maurer, Jr. et al.
6,565,554 B1 5/2003 Niemeyer
6,587,750 B2 7/2003 Gerbi et al.
6,614,453 B1 9/2003 Suri et al.
6,614,871 B1 9/2003 Kobiki et al.
6,619,840 B2 9/2003 Rasche et al.
6,636,757 B1 10/2003 Jascob et al.
6,645,196 B1 11/2003 Nixon et al.
6,666,579 B2 12/2003 Jensen
6,669,635 B2 12/2003 Kessman et al.
6,701,173 B2 3/2004 Nowinski et al.
6,757,068 B2 6/2004 Foxlin
6,782,287 B2 8/2004 Grzeszczuk et al.
6,783,524 B2 8/2004 Anderson et al.
6,786,896 B1 9/2004 Madhani et al.
6,788,018 B1 9/2004 Blumenkranz
6,804,581 B2 10/2004 Wang et al.
6,823,207 B1 11/2004 Jensen et al.
6,827,351 B2 12/2004 Graziani et al.
6,837,892 B2 1/2005 Shoham
6,839,612 B2 1/2005 Sanchez et al.
6,856,826 B2 2/2005 Seeley et al.
6,856,827 B2 2/2005 Seeley et al.
6,879,880 B2 4/2005 Nowlin et al.
6,892,090 B2 5/2005 Verard et al.
6,920,347 B2 7/2005 Simon et al.
6,922,632 B2 7/2005 Foxlin
6,968,224 B2 11/2005 Kessman et al.
6,978,166 B2 12/2005 Foley et al.
6,988,009 B2 1/2006 Grimm et al.
6,991,627 B2 1/2006 Madhani et al.
6,996,487 B2 2/2006 Jutras et al.
6,999,852 B2 2/2006 Green
7,007,699 B2 3/2006 Martinelli et al.
7,016,457 B1 3/2006 Senzig et al.
7,043,961 B2 5/2006 Pandey et al.
7,062,006 B1 6/2006 Pelc et al.
7,063,705 B2 6/2006 Young et al.
7,072,707 B2 7/2006 Galloway, Jr. et al.
7,083,615 B2 8/2006 Peterson et al.
7,097,640 B2 8/2006 Wang et al.
7,099,428 B2 8/2006 Clinthorne et al.
7,108,421 B2 9/2006 Gregerson et al.
7,130,676 B2 10/2006 Barrick
7,139,418 B2 11/2006 Abovitz et al.
7,139,601 B2 11/2006 Bucholz et al.
7,155,316 B2 12/2006 Sutherland et al.
7,164,968 B2 1/2007 Treat et al.
7,167,738 B2 1/2007 Schweikard et al.
7,169,141 B2 1/2007 Brock et al.
7,172,627 B2 2/2007 Fiere et al.
7,194,120 B2 3/2007 Wicker et al.
7,197,107 B2 3/2007 Arai et al.
7,231,014 B2 6/2007 Levy
7,231,063 B2 6/2007 Naimark et al.
7,239,940 B2 7/2007 Wang et al.
7,248,914 B2 7/2007 Hastings et al.
7,301,648 B2 11/2007 Foxlin
7,302,288 B1 11/2007 Schellenberg
7,313,430 B2 12/2007 Urquhart et al.
7,318,805 B2 1/2008 Schweikard et al.
7,318,827 B2 1/2008 Leitner et al.
7,319,897 B2 1/2008 Leitner et al.
7,324,623 B2 1/2008 Heuscher et al.
7,327,865 B2 2/2008 Fu et al.
7,331,967 B2 2/2008 Lee et al.
7,333,642 B2 2/2008 Green
7,339,341 B2 3/2008 Oleynikov et al.
7,366,562 B2 4/2008 Dukesherer et al.
7,379,790 B2 5/2008 Toth et al.
7,386,365 B2 6/2008 Nixon
7,422,592 B2 9/2008 Morley et al.
7,435,216 B2 10/2008 Kwon et al.
7,440,793 B2 10/2008 Chauhan et al.
7,460,637 B2 12/2008 Clinthorne et al.
7,466,303 B2 12/2008 Yi et al.
7,493,153 B2 2/2009 Ahmed et al.
7,505,617 B2 3/2009 Fu et al.
7,533,892 B2 5/2009 Schena et al.
7,542,791 B2 6/2009 Mire et al.
7,555,331 B2 6/2009 Viswanathan
7,567,834 B2 7/2009 Clayton et al.
7,594,912 B2 9/2009 Cooper et al.
7,606,613 B2 10/2009 Simon et al.
7,607,440 B2 10/2009 Coste-Maniere et al.
7,623,902 B2 11/2009 Pacheco
7,630,752 B2 12/2009 Viswanathan
7,630,753 B2 12/2009 Simon et al.
7,643,862 B2 1/2010 Schoenefeld
7,660,623 B2 2/2010 Hunter et al.
7,661,881 B2 2/2010 Gregerson et al.
7,683,331 B2 3/2010 Chang
7,683,332 B2 3/2010 Chang
7,689,320 B2 3/2010 Prisco et al.
7,691,098 B2 4/2010 Wallace et al.
7,702,379 B2 4/2010 Avinash et al.
7,702,477 B2 4/2010 Tuemmler et al.
7,711,083 B2 5/2010 Heigl et al.
7,711,406 B2 5/2010 Kuhn et al.
7,720,523 B2 5/2010 Omernick et al.
7,725,253 B2 5/2010 Foxlin
7,726,171 B2 6/2010 Langlotz et al.
7,742,801 B2 6/2010 Neubauer et al.
7,751,865 B2 7/2010 Jascob et al.
7,760,849 B2 7/2010 Zhang
7,762,825 B2 7/2010 Burbank et al.
7,763,015 B2 7/2010 Cooper et al.
7,787,699 B2 8/2010 Mahesh et al.
7,796,728 B2 9/2010 Bergfjord
7,813,838 B2 10/2010 Sommer
7,818,044 B2 10/2010 Dukesherer et al.
7,819,859 B2 10/2010 Prisco et al.
7,824,401 B2 11/2010 Manzo et al.
7,831,294 B2 11/2010 Viswanathan
7,834,484 B2 11/2010 Sartor
7,835,557 B2 11/2010 Kendrick et al.
7,835,778 B2 11/2010 Foley et al.
7,835,784 B2 11/2010 Mire et al.
7,840,253 B2 11/2010 Tremblay et al.
7,840,256 B2 11/2010 Lakin et al.
7,843,158 B2 11/2010 Prisco

(56) References Cited

U.S. PATENT DOCUMENTS 7,844,320 B2 11/2010 Shahidi
7,853,305 B2 12/2010 Simon et al.
7,853,313 B2 12/2010 Thompson
7,865,269 B2 1/2011 Prisco et al.
D631,966 S 2/2011 Perloff et al.
7,879,045 B2 2/2011 Gielen et al.
7,881,767 B2 2/2011 Strommer et al.
7,881,770 B2 2/2011 Melkent et al.
7,886,743 B2 2/2011 Cooper et al.
RE42,194 E 3/2011 Foley et al.
RE42,226 E 3/2011 Foley et al.
7,900,524 B2 3/2011 Calloway et al.
7,907,166 B2 3/2011 Lamprecht et al.
7,909,122 B2 3/2011 Schena et al.
7,925,653 B2 4/2011 Saptharishi
7,930,065 B2 4/2011 Larkin et al.
7,935,130 B2 5/2011 Willliams
7,940,999 B2 5/2011 Liao et al.
7,945,012 B2 5/2011 Ye et al.
7,945,021 B2 5/2011 Shapiro et al.
7,953,470 B2 5/2011 Vetter et al.
7,954,397 B2 6/2011 Choi et al.
7,971,341 B2 7/2011 Dukesherer et al.
7,974,674 B2 7/2011 Hauck et al.
7,974,677 B2 7/2011 Mire et al.
7,974,681 B2 7/2011 Wallace et al.
7,979,157 B2 7/2011 Anvari
7,983,733 B2 7/2011 Viswanathan
7,988,215 B2 8/2011 Seibold
7,996,110 B2 8/2011 Lipow et al.
8,004,121 B2 8/2011 Sartor
8,004,229 B2 8/2011 Nowlin et al.
8,010,177 B2 8/2011 Csavoy et al.
8,019,045 B2 9/2011 Kato
8,021,310 B2 9/2011 Sanborn et al.
8,035,685 B2 10/2011 Jensen
8,046,054 B2 10/2011 Kim et al.
8,046,057 B2 10/2011 Clarke
8,052,688 B2 11/2011 Wolf, II
8,054,184 B2 11/2011 Cline et al.
8,054,752 B2 11/2011 Druke et al.
8,057,397 B2 11/2011 Li et al.
8,057,407 B2 11/2011 Martinelli et al.
8,062,288 B2 11/2011 Cooper et al.
8,062,375 B2 11/2011 Glerum et al.
8,066,524 B2 11/2011 Burbank et al.
8,073,335 B2 12/2011 Labonville et al.
8,079,950 B2 12/2011 Stern et al.
8,086,299 B2 12/2011 Adler et al.
8,092,370 B2 1/2012 Roberts et al.
8,098,914 B2 1/2012 Liao et al.
8,100,950 B2 1/2012 St. Clair et al.
8,105,320 B2 1/2012 Manzo
8,108,025 B2 1/2012 Csavoy et al.
8,109,877 B2 2/2012 Moctezuma de la Barrera et al.
8,112,292 B2 2/2012 Simon
8,116,430 B1 2/2012 Shapiro et al.
8,120,301 B2 2/2012 Goldberg et al.
8,121,249 B2 2/2012 Wang et al.
8,123,675 B2 2/2012 Funda et al.
8,133,229 B1 3/2012 Bonutti
8,142,420 B2 3/2012 Schena
8,147,494 B2 4/2012 Leitner et al.
8,150,494 B2 4/2012 Simon et al.
8,150,497 B2 4/2012 Gielen et al.
8,150,498 B2 4/2012 Gielen et al.
8,165,658 B2 4/2012 Waynik et al.
8,170,313 B2 5/2012 Kendrick et al.
8,179,073 B2 5/2012 Farritor et al.
8,182,476 B2 5/2012 Julian et al.
8,184,880 B2 5/2012 Zhao et al.
8,202,278 B2 6/2012 Orban, III et al.
8,208,708 B2 6/2012 Homan et al.
8,208,988 B2 6/2012 Jensen
8,219,177 B2 7/2012 Smith et al.
8,219,178 B2 7/2012 Smith et al.
8,220,468 B2 7/2012 Cooper et al.
8,224,024 B2 7/2012 Foxlin et al.
8,224,484 B2 7/2012 Swarup et al.
8,225,798 B2 7/2012 Baldwin et al.
8,228,368 B2 7/2012 Zhao et al.
8,231,610 B2 7/2012 Jo et al.
8,239,001 B2 8/2012 Verard et al.
8,241,271 B2 8/2012 Millman et al.
8,248,413 B2 8/2012 Gattani et al.
8,256,319 B2 9/2012 Cooper et al.
8,263,933 B2 9/2012 Zeile
8,271,069 B2 9/2012 Jascob et al.
8,271,130 B2 9/2012 Hourtash
8,281,670 B2 10/2012 Larkin et al.
8,282,653 B2 10/2012 Nelson et al.
8,301,226 B2 10/2012 Csavoy et al.
8,311,611 B2 11/2012 Csavoy et al.
8,320,991 B2 11/2012 Jascob et al.
8,332,012 B2 12/2012 Kienzle, III
8,333,755 B2 12/2012 Cooper et al.
8,335,552 B2 12/2012 Stiles
8,335,557 B2 12/2012 Maschke
8,348,931 B2 1/2013 Cooper et al.
8,353,963 B2 1/2013 Glerum
8,358,818 B2 1/2013 Miga et al.
8,359,730 B2 1/2013 Burg et al.
8,374,673 B2 2/2013 Adcox et al.
8,374,723 B2 2/2013 Zhao et al.
8,379,791 B2 2/2013 Forthmann et al.
8,386,019 B2 2/2013 Camus et al.
8,392,022 B2 3/2013 Ortmaier et al.
8,394,099 B2 3/2013 Patwardhan
8,395,342 B2 3/2013 Prisco
8,398,634 B2 3/2013 Manzo et al.
8,400,094 B2 3/2013 Schena
8,414,957 B2 4/2013 Enzerink et al.
8,418,073 B2 4/2013 Mohr et al.
8,450,694 B2 5/2013 Baviera et al.
8,452,447 B2 5/2013 Nixon
RE44,305 E 6/2013 Foley et al.
8,462,911 B2 6/2013 Vesel et al.
8,465,476 B2 6/2013 Rogers et al.
8,465,771 B2 6/2013 Wan et al.
8,467,851 B2 6/2013 Mire et al.
8,467,852 B2 6/2013 Csavoy et al.
8,469,947 B2 6/2013 Devengenzo et al.
RE44,392 E 7/2013 Hynes
8,483,434 B2 7/2013 Buehner et al.
8,483,800 B2 7/2013 Jensen et al.
8,486,532 B2 7/2013 Enzerink et al.
8,489,235 B2 7/2013 Moll et al.
8,500,722 B2 8/2013 Cooper
8,500,728 B2 8/2013 Newton et al.
8,504,201 B2 8/2013 Moll et al.
8,506,555 B2 8/2013 Ruiz Morales
8,506,556 B2 8/2013 Schena
8,508,173 B2 8/2013 Goldberg et al.
8,512,318 B2 8/2013 Tovey et al.
8,515,576 B2 8/2013 Lipow et al.
8,518,120 B2 8/2013 Glerum et al.
8,521,331 B2 8/2013 Itkowitz
8,526,688 B2 9/2013 Groszmann et al.
8,526,700 B2 9/2013 Issacs
8,527,094 B2 9/2013 Kumar et al.
8,528,440 B2 9/2013 Morley et al.
8,532,741 B2 9/2013 Heruth et al.
8,541,970 B2 9/2013 Nowlin et al.
8,548,563 B2 10/2013 Simon et al.
8,549,732 B2 10/2013 Burg et al.
8,551,114 B2 10/2013 Ramos de la Pena
8,551,116 B2 10/2013 Julian et al.
8,556,807 B2 10/2013 Scott et al.
8,556,979 B2 10/2013 Glerum et al.
8,560,118 B2 10/2013 Green et al.
8,561,473 B2 10/2013 Blumenkranz
8,562,594 B2 10/2013 Cooper et al.
8,571,638 B2 10/2013 Shoham
8,571,710 B2 10/2013 Coste-Maniere et al.

(56) References Cited

U.S. PATENT DOCUMENTS 8,573,465 B2 11/2013 Shelton, IV
8,574,303 B2 11/2013 Sharkey et al.
8,585,420 B2 11/2013 Burbank et al.
8,594,841 B2 11/2013 Zhao et al.
8,597,198 B2 12/2013 Sanborn et al.
8,600,478 B2 12/2013 Verard et al.
8,603,077 B2 12/2013 Cooper et al.
8,611,985 B2 12/2013 Lavallee et al.
8,613,230 B2 12/2013 Blumenkranz et al.
8,621,939 B2 1/2014 Blumenkranz et al.
8,624,537 B2 1/2014 Nowlin et al.
8,630,389 B2 1/2014 Kato
8,634,897 B2 1/2014 Simon et al.
8,634,957 B2 1/2014 Toth et al.
8,638,056 B2 1/2014 Goldberg et al.
8,638,057 B2 1/2014 Goldberg et al.
8,639,000 B2 1/2014 Zhao et al.
8,641,726 B2 2/2014 Bonutti
8,644,907 B2 2/2014 Hartmann et al.
8,657,809 B2 2/2014 Schoepp
8,660,635 B2 2/2014 Simon et al.
8,666,544 B2 3/2014 Moll et al.
8,675,939 B2 3/2014 Moctezuma de la Barrera
8,678,647 B2 3/2014 Gregerson et al.
8,679,125 B2 3/2014 Smith et al.
8,679,183 B2 3/2014 Glerum et al.
8,682,413 B2 3/2014 Lloyd
8,684,253 B2 4/2014 Giordano et al.
8,685,098 B2 4/2014 Glerum et al.
8,693,730 B2 4/2014 Umasuthan et al.
8,694,075 B2 4/2014 Groszmann et al.
8,696,458 B2 4/2014 Foxlin et al.
8,700,123 B2 4/2014 Okamura et al.
8,706,086 B2 4/2014 Glerum
8,706,185 B2 4/2014 Foley et al.
8,706,301 B2 4/2014 Zhao et al.
8,717,430 B2 5/2014 Simon et al.
8,727,618 B2 5/2014 Maschke et al.
8,734,432 B2 5/2014 Tuma et al.
8,738,115 B2 5/2014 Amberg et al.
8,738,181 B2 5/2014 Greer et al.
8,740,882 B2 6/2014 Jun et al.
8,746,252 B2 6/2014 McGrogan et al.
8,749,189 B2 6/2014 Nowlin et al.
8,749,190 B2 6/2014 Nowlin et al.
8,761,930 B2 6/2014 Nixon
8,764,448 B2 7/2014 Yang et al.
8,771,170 B2 7/2014 Mesallum et al.
8,781,186 B2 7/2014 Clements et al.
8,781,630 B2 7/2014 Banks et al.
8,784,385 B2 7/2014 Boyden et al.
8,786,241 B2 7/2014 Nowlin et al.
8,787,520 B2 7/2014 Baba
8,792,704 B2 7/2014 Isaacs
8,798,231 B2 8/2014 Notohara et al.
8,800,838 B2 8/2014 Shelton, IV
8,808,164 B2 8/2014 Hoffman et al.
8,812,077 B2 8/2014 Dempsey
8,814,793 B2 8/2014 Brabrand
8,816,628 B2 8/2014 Nowlin et al.
8,818,105 B2 8/2014 Myronenko et al.
8,820,605 B2 9/2014 Shelton, IV
8,821,511 B2 9/2014 von Jako et al.
8,823,308 B2 9/2014 Nowlin et al.
8,827,996 B2 9/2014 Scott et al.
8,828,024 B2 9/2014 Farritor et al.
8,830,224 B2 9/2014 Zhao et al.
8,834,489 B2 9/2014 Cooper et al.
8,834,490 B2 9/2014 Bonutti
8,838,270 B2 9/2014 Druke et al.
8,844,789 B2 9/2014 Shelton, IV et al.
8,855,822 B2 10/2014 Bartol et al.
8,858,598 B2 10/2014 Seifert et al.
8,860,753 B2 10/2014 Bhandarkar et al.
8,864,751 B2 10/2014 Prisco et al.
8,864,798 B2 10/2014 Weiman et al.
8,864,833 B2 10/2014 Glerum et al.
8,867,703 B2 10/2014 Shapiro et al.
8,870,880 B2 10/2014 Himmelberger et al.
8,876,866 B2 11/2014 Zappacosta et al.
8,880,223 B2 11/2014 Raj et al.
8,882,803 B2 11/2014 Iott et al.
8,883,210 B1 11/2014 Truncale et al.
8,888,821 B2 11/2014 Rezach et al.
8,888,853 B2 11/2014 Glerum et al.
8,888,854 B2 11/2014 Glerum et al.
8,894,652 B2 11/2014 Seifert et al.
8,894,688 B2 11/2014 Suh
8,894,691 B2 11/2014 Iott et al.
8,906,069 B2 12/2014 Hansell et al.
8,964,934 B2 2/2015 Ein-Gal
8,992,580 B2 3/2015 Bar et al.
8,996,169 B2 3/2015 Lightcap et al.
9,001,963 B2 4/2015 Sowards-Emmerd et al.
9,002,076 B2 4/2015 Khadem et al.
9,044,190 B2 6/2015 Rubner et al.
9,107,683 B2 8/2015 Hourtash et al.
9,125,556 B2 9/2015 Zehavi et al.
9,131,986 B2 9/2015 Greer et al.
9,215,968 B2 12/2015 Schostek et al.
9,308,050 B2 4/2016 Kostrzewski et al.
9,380,984 B2 7/2016 Li et al.
9,393,039 B2 7/2016 Lechner et al.
9,398,886 B2 7/2016 Gregerson et al.
9,398,890 B2 7/2016 Dong et al.
9,414,859 B2 8/2016 Ballard et al.
9,420,975 B2 8/2016 Gutfleisch et al.
9,492,235 B2 11/2016 Hourtash et al.
9,592,096 B2 3/2017 Maillet et al.
9,750,465 B2 9/2017 Engel et al.
9,757,203 B2 9/2017 Hourtash et al.
9,795,354 B2 10/2017 Menegaz et al.
9,814,535 B2 11/2017 Bar et al.
9,820,783 B2 11/2017 Donner et al.
9,833,265 B2 12/2017 Donner et al.
9,848,922 B2 12/2017 Tohmeh et al.
9,925,011 B2 3/2018 Gombert et al.
9,931,025 B1 4/2018 Graetzel et al.
10,034,717 B2 7/2018 Miller et al.
2001/0036302 A1 11/2001 Miller
2002/0035321 A1 3/2002 Bucholz et al.
2004/0068172 A1 4/2004 Nowinski et al.
2004/0076259 A1 4/2004 Jensen et al.
2005/0096502 A1 5/2005 Khalili
2005/0143651 A1 6/2005 Verard et al.
2005/0171558 A1 8/2005 Abovitz et al.
2006/0015018 A1* 1/2006 Jutras .................... A61B 34/20
600/301
2006/0100610 A1 5/2006 Wallace et al.
2006/0173329 A1 8/2006 Marquart et al.
2006/0184396 A1 8/2006 Dennis et al.
2006/0241416 A1 10/2006 Marquart et al.
2006/0291612 A1 12/2006 Nishide et al.
2007/0015987 A1 1/2007 Benlloch Baviera et al.
2007/0021738 A1 1/2007 Hasser et al.
2007/0038059 A1 2/2007 Sheffer et al.
2007/0073133 A1 3/2007 Schoenefeld
2007/0156121 A1 7/2007 Millman et al.
2007/0156157 A1 7/2007 Nahum et al.
2007/0167712 A1 7/2007 Keglovich et al.
2007/0233238 A1 10/2007 Huynh et al.
2008/0004523 A1 1/2008 Jensen
2008/0013809 A1 1/2008 Zhu et al.
2008/0033283 A1 2/2008 Dellaca et al.
2008/0046122 A1 2/2008 Manzo et al.
2008/0082109 A1 4/2008 Moll et al.
2008/0108912 A1 5/2008 Node-Langlois
2008/0108991 A1 5/2008 von Jako
2008/0109012 A1 5/2008 Falco et al.
2008/0144906 A1 6/2008 Allred et al.
2008/0161680 A1 7/2008 von Jako et al.
2008/0161682 A1 7/2008 Kendrick et al.
2008/0177203 A1 7/2008 von Jako
2008/0214922 A1 9/2008 Hartmann et al.

(56) References Cited

U.S. PATENT DOCUMENTS

2008/0228068 A1 9/2008 Viswanathan et al.
2008/0228196 A1 9/2008 Wang et al.
2008/0235052 A1 9/2008 Node-Langlois et al.
2008/0269596 A1 10/2008 Revie et al.
2008/0287771 A1 11/2008 Anderson
2008/0287781 A1 11/2008 Revie et al.
2008/0300477 A1 12/2008 Lloyd et al.
2008/0300478 A1 12/2008 Zuhars et al.
2008/0302950 A1 12/2008 Park et al.
2008/0306490 A1 12/2008 Lakin et al.
2008/0319311 A1 12/2008 Hamadeh
2009/0012509 A1 1/2009 Csavoy et al.
2009/0030428 A1 1/2009 Omori et al.
2009/0080737 A1 3/2009 Battle et al.
2009/0185655 A1 7/2009 Koken et al.
2009/0198121 A1 8/2009 Hoheisel
2009/0216113 A1 8/2009 Meier et al.
2009/0228019 A1 9/2009 Gross et al.
2009/0259123 A1 10/2009 Navab et al.
2009/0259230 A1 10/2009 Khadem et al.
2009/0264899 A1 10/2009 Appenrodt et al.
2009/0281417 A1 11/2009 Hartmann et al.
2010/0022874 A1 1/2010 Wang et al.
2010/0039506 A1 2/2010 Sarvestani et al.
2010/0125286 A1 5/2010 Wang et al.
2010/0130986 A1 5/2010 Mailloux et al.
2010/0228117 A1 9/2010 Hartmann
2010/0228265 A1 9/2010 Prisco
2010/0249571 A1 9/2010 Jensen et al.
2010/0274120 A1 10/2010 Heuscher
2010/0280363 A1 11/2010 Skarda et al.
2010/0331858 A1 12/2010 Simaan et al.
2011/0022229 A1 1/2011 Jang et al.
2011/0077504 A1 3/2011 Fischer et al.
2011/0098553 A1 4/2011 Robbins et al.
2011/0137152 A1 6/2011 Li
2011/0213384 A1 9/2011 Jeong
2011/0224684 A1 9/2011 Larkin et al.
2011/0224685 A1 9/2011 Larkin et al.
2011/0224686 A1 9/2011 Larkin et al.
2011/0224687 A1 9/2011 Larkin et al.
2011/0224688 A1 9/2011 Larkin et al.
2011/0224689 A1 9/2011 Larkin et al.
2011/0224825 A1 9/2011 Larkin et al.
2011/0230967 A1 9/2011 O'Halloran et al.
2011/0238080 A1 9/2011 Ranjit et al.
2011/0276058 A1 11/2011 Choi et al.
2011/0282189 A1 11/2011 Graumann
2011/0286573 A1 11/2011 Schretter et al.
2011/0295062 A1 12/2011 Gratacos Solsona et al.
2011/0295370 A1 12/2011 Suh et al.
2011/0306986 A1 12/2011 Lee et al.
2012/0035507 A1 2/2012 George et al.
2012/0046668 A1 2/2012 Gantes
2012/0051498 A1 3/2012 Koishi
2012/0053597 A1 3/2012 Anvari et al.
2012/0059248 A1 3/2012 Holsing et al.
2012/0071753 A1 3/2012 Hunter et al.
2012/0108954 A1 5/2012 Schulhauser et al.
2012/0136372 A1 5/2012 Amat Girbau et al.
2012/0143084 A1 6/2012 Shoham
2012/0184839 A1 7/2012 Woerlein
2012/0197182 A1 8/2012 Millman et al.
2012/0226145 A1 9/2012 Chang et al.
2012/0235909 A1 9/2012 Birkenbach et al.
2012/0245596 A1 9/2012 Meenink
2012/0253332 A1 10/2012 Moll
2012/0253360 A1 10/2012 White et al.
2012/0256092 A1 10/2012 Zingerman
2012/0294498 A1 11/2012 Popovic
2012/0296203 A1 11/2012 Hartmann et al.
2013/0006267 A1 1/2013 Odermatt et al.
2013/0016889 A1 1/2013 Myronenko et al.
2013/0030571 A1 1/2013 Ruiz Morales et al.
2013/0035583 A1 2/2013 Park et al.
2013/0060146 A1 3/2013 Yang et al.
2013/0060337 A1 3/2013 Petersheim et al.
2013/0094742 A1 4/2013 Feilkas
2013/0096574 A1 4/2013 Kang et al.
2013/0113791 A1 5/2013 Isaacs et al.
2013/0116706 A1 5/2013 Lee et al.
2013/0131695 A1 5/2013 Scarfogliero et al.
2013/0144307 A1 6/2013 Jeong et al.
2013/0158542 A1 6/2013 Manzo et al.
2013/0165937 A1 6/2013 Patwardhan
2013/0178867 A1 7/2013 Farritor et al.
2013/0178868 A1 7/2013 Roh
2013/0178870 A1 7/2013 Schena
2013/0204271 A1 8/2013 Brisson et al.
2013/0211419 A1 8/2013 Jensen
2013/0211420 A1 8/2013 Jensen
2013/0218142 A1 8/2013 Tuma et al.
2013/0223702 A1 8/2013 Holsing et al.
2013/0225942 A1 8/2013 Holsing et al.
2013/0225943 A1 8/2013 Holsing et al.
2013/0231556 A1 9/2013 Holsing et al.
2013/0237995 A1 9/2013 Lee et al.
2013/0245375 A1 9/2013 DiMaio et al.
2013/0261640 A1 10/2013 Kim et al.
2013/0272488 A1 10/2013 Bailey et al.
2013/0272489 A1 10/2013 Dickman et al.
2013/0274761 A1 10/2013 Devengenzo et al.
2013/0281821 A1 10/2013 Liu et al.
2013/0296884 A1 11/2013 Taylor et al.
2013/0303887 A1 11/2013 Holsing et al.
2013/0307955 A1 11/2013 Deitz et al.
2013/0317521 A1 11/2013 Choi et al.
2013/0325033 A1 12/2013 Schena et al.
2013/0325035 A1 12/2013 Hauck et al.
2013/0331686 A1 12/2013 Freysinger et al.
2013/0331858 A1 12/2013 Devengenzo et al.
2013/0331861 A1 12/2013 Yoon
2013/0342578 A1 12/2013 Isaacs
2013/0345717 A1 12/2013 Markvicka et al.
2013/0345757 A1 12/2013 Stad
2014/0001235 A1 1/2014 Shelton, IV
2014/0012131 A1 1/2014 Heruth et al.
2014/0031664 A1 1/2014 Kang et al.
2014/0046128 A1 2/2014 Lee et al.
2014/0046132 A1 2/2014 Hoeg et al.
2014/0046340 A1 2/2014 Wilson et al.
2014/0049629 A1 2/2014 Siewerdsen et al.
2014/0058406 A1 2/2014 Tsekos
2014/0073914 A1 3/2014 Lavallee et al.
2014/0080086 A1 3/2014 Chen
2014/0081128 A1 3/2014 Verard et al.
2014/0088612 A1 3/2014 Bartol et al.
2014/0094694 A1 4/2014 Moctezuma de la Barrera
2014/0094851 A1 4/2014 Gordon
2014/0096369 A1 4/2014 Matsumoto et al.
2014/0100587 A1 4/2014 Farritor et al.
2014/0121676 A1 5/2014 Kostrzewski et al.
2014/0128882 A1 5/2014 Kwak et al.
2014/0130810 A1 5/2014 Azizian et al.
2014/0135796 A1 5/2014 Simon et al.
2014/0142591 A1 5/2014 Alvarez et al.
2014/0142592 A1 5/2014 Moon et al.
2014/0148692 A1 5/2014 Hartmann et al.
2014/0163581 A1 6/2014 Devengenzo et al.
2014/0171781 A1 6/2014 Stiles
2014/0171900 A1 6/2014 Stiles
2014/0171965 A1 6/2014 Loh et al.
2014/0180308 A1 6/2014 von Grunberg
2014/0180309 A1 6/2014 Seeber et al.
2014/0187915 A1 7/2014 Yaroshenko et al.
2014/0188132 A1 7/2014 Kang
2014/0194699 A1 7/2014 Roh et al.
2014/0221819 A1 8/2014 Sarment
2014/0222023 A1 8/2014 Kim et al.
2014/0228631 A1 8/2014 Kwak et al.
2014/0234804 A1 8/2014 Huang et al.
2014/0257328 A1 9/2014 Kim et al.
2014/0257329 A1 9/2014 Jang et al.
2014/0257330 A1 9/2014 Choi et al.

(56) References Cited

U.S. PATENT DOCUMENTS

2014/0275760 A1 9/2014 Lee et al.
2014/0275985 A1 9/2014 Walker et al.
2014/0276931 A1 9/2014 Parihar et al.
2014/0276940 A1 9/2014 Seo
2014/0276944 A1 9/2014 Farritor et al.
2014/0288413 A1 9/2014 Hwang et al.
2014/0299648 A1 10/2014 Shelton, IV et al.
2014/0303434 A1 10/2014 Farritor et al.
2014/0303643 A1 10/2014 Ha et al.
2014/0305995 A1 10/2014 Shelton, IV et al.
2014/0309659 A1 10/2014 Roh et al.
2014/0316436 A1 10/2014 Bar et al.
2014/0323803 A1 10/2014 Hoffman et al.
2014/0324070 A1 10/2014 Min et al.
2014/0330288 A1 11/2014 Date et al.
2014/0364720 A1 12/2014 Darrow et al.
2014/0371577 A1 12/2014 Maillet et al.
2015/0039034 A1 2/2015 Frankel et al.
2015/0085970 A1 3/2015 Bouhnik et al.
2015/0146847 A1 5/2015 Liu
2015/0150524 A1 6/2015 Yorkston et al.
2015/0182236 A1* 7/2015 Dardenne .............. A61B 17/17 606/281
2015/0196261 A1 7/2015 Funk
2015/0213633 A1 7/2015 Chang et al.
2015/0335480 A1 11/2015 Alvarez et al.
2015/0342647 A1 12/2015 Frankel et al.
2016/0005194 A1 1/2016 Schretter et al.
2016/0166329 A1 6/2016 Langan et al.
2016/0235480 A1 8/2016 Scholl et al.
2016/0249990 A1 9/2016 Glozman et al.
2016/0302871 A1 10/2016 Gregerson et al.
2016/0320322 A1 11/2016 Suzuki
2016/0331335 A1 11/2016 Gregerson et al.
2017/0135770 A1 5/2017 Scholl et al.
2017/0143284 A1 5/2017 Sehnert et al.
2017/0143426 A1 5/2017 Isaacs et al.
2017/0156816 A1 6/2017 Ibrahim
2017/0202629 A1 7/2017 Maillet et al.
2017/0212723 A1 7/2017 Atarot et al.
2017/0215825 A1 8/2017 Johnson et al.
2017/0215826 A1 8/2017 Johnson et al.
2017/0215827 A1 8/2017 Johnson et al.
2017/0231710 A1 8/2017 Scholl et al.
2017/0258426 A1 9/2017 Risher-Kelly et al.
2017/0273748 A1 9/2017 Hourtash et al.
2017/0296277 A1 10/2017 Hourtash et al.
2017/0360493 A1 12/2017 Zucher et al.
2020/0383803 A1* 12/2020 Wu ...................... A61B 6/5217
2021/0369535 A1* 12/2021 Ishimine .............. A61H 1/0288

* cited by examiner

Figure 4:
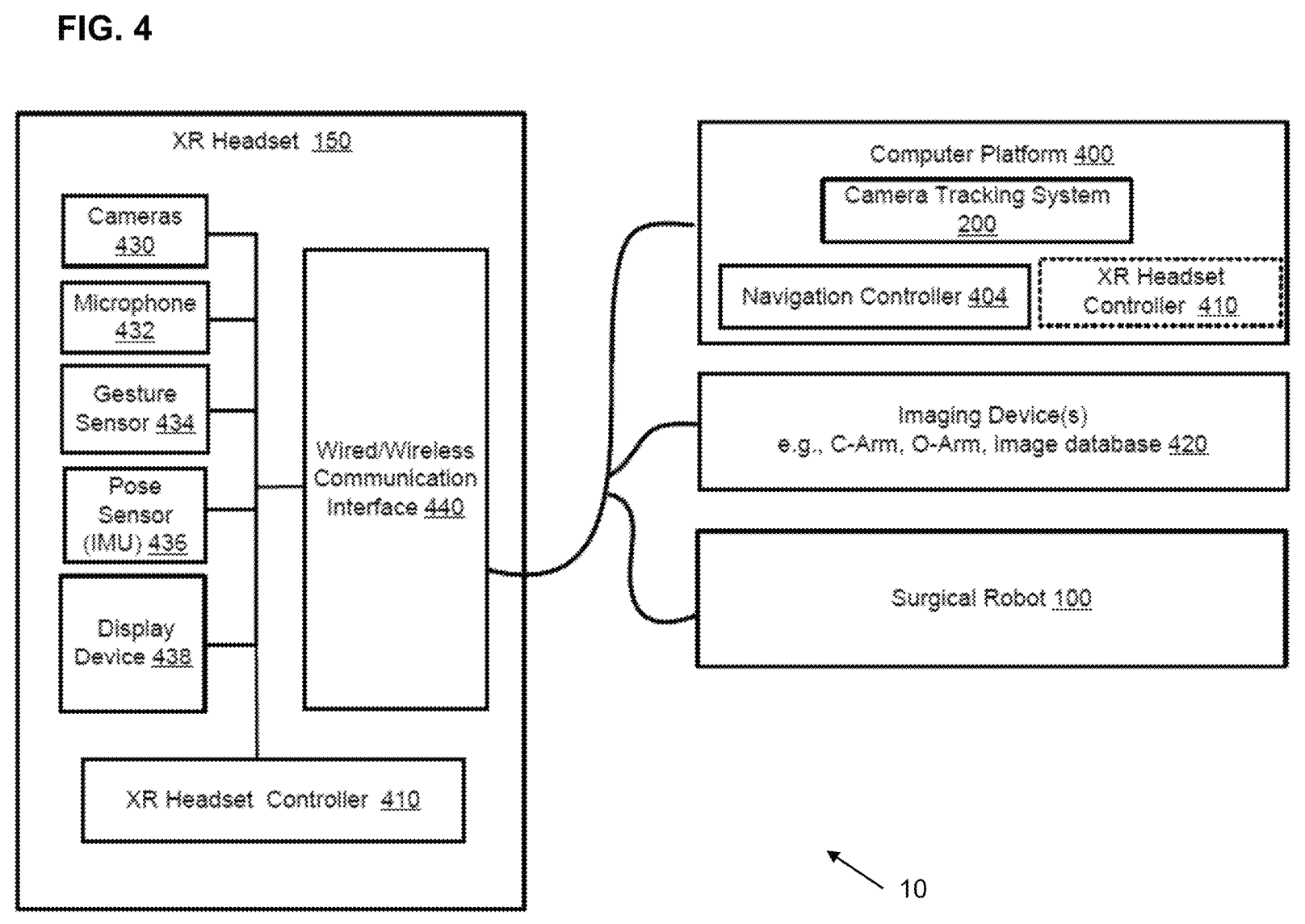

Computer Platform 400
Camera Tracking System 200
Navigation Controller 404
XR Headset Controller 410
Imaging Device(s) e.g., C-Arm, O-Arm, image database 420
Surgical Robot 100
10
XR Headset 150
Wired/Wireless Communication Interface 440
Cameras 430
Microphone 432
Gesture Sensor 434
Pose Sensor (IMU) 436
Display Device 438
XR Headset Controller 410

FIG. 8

TRANSVERSE PLANE

SAGITAL PLANE

Z AXIS (SUPERIOR INFERIOR AXIS)

A1

A2

CUP NORMAL AXIS

CORONAL PLANE

A2

CORONAL PLANE

DYNAMIC REFERENCE BASE FOR ROBOTIC-ASSISTED TOTAL HIP ARTHROPLASTY

BACKGROUND OF THE DISCLOSURE

The invention relates generally to devices, systems, and methods for use in robot-assisted surgical procedures. More particularly, the invention relates to a dynamic reference base adapted for use in tracking a location of one or more bones during navigated or robot-assisted total hip arthroplasty (THA) surgery.

Hip arthroplasty, or hip replacement, is a surgical procedure used to resurface and reconstruct a hip joint that has been damaged by disease or injury, e.g., by arthritis or a fracture. THA devices replace both the acetabulum and the femoral head that collectively comprise the hip joint. An acetabular implant is secured to the acetabulum, forming a replacement articulating surface which interfaces with the femoral implant secured to the end of the femur. The femoral implant is pivotably coupled to the acetabular implant, thereby reconstructing the hip joint. Exemplary acetabular implants are disclosed in, e.g., U.S. patent application Ser. No. 17/024,876, filed Sep. 18, 2020 (published as US 2022/0087823 A1), which is incorporated by reference as though fully set forth herein.

Robotic surgery systems including computer-assisted navigation have become a well-established technique in operating rooms, including their use in arthroplasty procedures. Computer-assisted navigation systems provide surgeons with computerized visualization of how a surgical instrument or other device that is posed relative to a patient correlates to a pose relative to medical images of the patient's anatomy, and how those poses correlate to a pre-operative surgical plan. Camera tracking systems for computer assisted surgery navigation typically use a set of tracking cameras to track a pose of a reference element on the surgical instrument, which may be coupled to a surgical robot and may be positioned by a surgeon during surgery, relative to a patient reference element (or "dynamic reference base" (DRB)) affixed to the patient. A computer model of a real instrument is associated with a reference element, so that the computer model can be overlaid on registered images of patient's anatomy. The camera tracking system uses the relative poses of the reference elements to determine how the real instrument is posed relative to the patient and to determine how the computer model of the real instrument is to be correspondingly posed as overlaid on the medical images. The surgeon can thereby use real-time visual feedback of the relative poses to navigate the surgical instrument during a surgical procedure on the patient.

As noted above, a robotic system may be used for arthroplasty procedures. The robotic system (or, "robot" or "surgical robot") has a serial arm on which an end effector is mounted. The surgeon (or "user") may hold the end effector or any instruments coupled thereto, to perform surgical operations while watching in real time on a navigation system (e.g., on stand-alone display(s) or an Augmented Reality (AR) headset), and to receive various types of relevant feedback and information associated with a defined plan for and/or progress of the surgical procedure.

The serial arm can move through computer guided control to a suitable position for the surgery, e.g., pursuant to the surgeon's request, which may be provided via a foot pedal, touchscreen, AR interaction, etc. The passive robotic structure allows the surgeon to precisely perform each operation in the procedure.

Various workflows may be available for use with the system. Such workflows may incorporate preoperative scans or images of the patient (e.g., x-ray or Computerized Tomography (CT)). On the other hand, other workflows may be imageless, and may not require any pre-operative images. Some workflows may incorporate acquisition of intra-operative information about the patient anatomy. In one example, the surgeon may measure key parameters of the bone using a camera tracking system and an appropriate tracked instrument to capture points on patient anatomy. Later, this information, and other intra-operatively-acquired information may be used to plan the implant position and orientation with respect to patient anatomy, and to navigate the robot and surgical instruments during the surgical procedure.

In some workflows, the surgeon may rigidly attach a reference element to one or more bones, where the reference element includes fiducials which are detected by tracking cameras for computer assisted navigation. The reference elements allow tracking of bone position by the navigation system. The reference elements can be positioned on the bone and oriented such that they can be seen by the tracking cameras of the navigation system. Once positioned, the reference elements are attached with fixation structures (e.g., screw pins, "crocodile" jaws) on the bone (e.g., pelvis or femur). The reference elements' respective positions and orientations stay rigidly fixed with respect to the bone throughout the procedure.

Another process of various workflows is to register the patient in the tracking space of the navigation system. Patient registration can include matching the patient anatomy with a numeric representation of the corresponding bone, such as a three-dimensional (3D) model of the bone. The bone representation may be constructed from, e.g., a set of CT images (CT workflow), a set of fluoroscopy images, or based on a generic bone model (imageless workflow).

Although current approaches to rigidly connecting markers to bone to track intra-operative bone position offer the ability to perform sophisticated navigated and robot-assisted surgeries, existing reference elements have certain shortcomings. For example, different devices may be required depending on the patient's position on the operating table, and/or the side of the patient on which the target surgical area is located.

BRIEF DESCRIPTION OF THE DISCLOSURE

A first aspect of the disclosure provides a dynamic reference base (DRB) comprising: a bridge element including a connecting rod having a distal end and a proximal end, a clamp coupled to the distal end of the connecting rod, a first clutch coupled to the proximal end of the connecting rod, the first clutch being adapted to couple to an array frame, a first and a second pin guide extending distally from the clamp, and a locking nut disposed on the clamp and adapted to tighten the bridge element to a bone pin disposed within each of the first and second pin guides; and the array frame affixed to the first clutch.

In certain embodiments, the bridge element further comprises a second clutch, and the first clutch and the second clutch are separated by an angle of about 45° to about 135° or preferably about 45° to about 90°.

In certain embodiments, the connecting rod further includes: a first portion located at the distal end thereof, extending perpendicularly relative to the first and second pin guides, a first bend, transitioning from the first portion to a second portion extending proximally, away from a direction of the first and second pin guides; and a second bend between the second portion and a third, proximal-most portion, wherein the third, proximal-most portion extends at an angle of about 30 to about 60 degrees relative to a plane defined by the first and second pin guides.

In certain embodiments, the first and second pin guides are integrated with the clamp.

In certain embodiments, the array frame comprises: a first rotatable coupling secured thereto, and secured in rotational position by a locking nut; and a second rotatable coupling secured to the first rotatable coupling, the second rotatable coupling including a captured screw adapted to be received in the first clutch, wherein the first rotatable coupling is adapted to rotate about an axis that is approximately perpendicular to an axis about which the second rotatable coupling is adapted to rotate.

In certain embodiments, a plurality of markers is disposed on the array frame.

In certain embodiments, a bone pin is disposed in each of the first and second pin guides.

In certain embodiments, each bone pin is adapted for insertion into a pelvis of a patient.

A second aspect of the disclosure provides a method for affixing a dynamic reference base (DRB) to a patient, comprising: providing an array frame and a bridge element including a connecting rod having a distal end and a proximal end, a clamp coupled to the distal end of the connecting rod, a clutch coupled to the proximal end of the connecting rod, the clutch being adapted to couple to the array frame, a first and a second pin guide extending distally from the clamp, and a locking nut disposed on the clamp; inserting the first pin guide over the first bone pin; inserting the second bone pin through the second pin guide; tightening the locking nut to secure the bridge element to the first and the second bone pins; coupling the array frame to the clutch; adjusting a position of the array frame relative to a first axis and a second axis in a defined coordinate system; and locking the array frame into place relative to the bridge element.

In certain embodiments, the method further includes attaching tracking markers to the array frame.

In certain embodiments, the method includes, prior to inserting the first pin guide over the first bone pin, making a first incision in the patient's skin; and inserting the first bone pin through the first incision into a pelvis of the patient.

In certain embodiments, the method includes, after inserting the first pin guide over the first bone pin, and prior to inserting the second bone pin through the second pin guide, using the position of the second pin guide to mark a location for a second incision; and making the second incision on the patient's skin.

In certain embodiments, inserting the second bone pin further comprises inserting the second bone pin into an iliac crest of the patient.

In certain embodiments, the array frame comprises: a first rotatable coupling secured thereto and rotatable about a first axis, and securable in rotational position by a locking nut; and a second rotatable coupling secured to the first rotatable coupling and rotatable about a second axis, the second rotatable coupling including a captured screw adapted to be received in the clutch. In such embodiments, coupling the array frame to the clutch comprises at least partially threading the captured screw into the clutch of the bridge element.

In certain embodiments, adjusting the position of the array frame further comprises: rotating the second rotatable coupling about the second axis; and rotating the first rotatable coupling about the first axis, wherein the first axis and the second axis are approximately perpendicular to one another.

In certain embodiments, locking the array frame into position relative to the bridge element further comprises tightening the captured screw of the second rotatable coupling and the locking nut of the first rotatable coupling.

In certain embodiments, after adjusting the position of the array frame, the method includes confirming that the array frame is visible to a tracking camera.

In certain embodiments, the clutch of the bridge element is one of a pair of clutches coupled to the proximal end of the connecting rod, each clutch of the pair of clutches being adapted to couple to the array frame, wherein the pair of clutches are separated from one another by an angle of about 45° to about 135° or preferably about 45° to about 90°. Coupling the array frame to the clutch further comprises selecting one clutch from the pair of clutches, based in part on one or more of: whether the dynamic reference base is affixed to a left or a right side of the patient, a location of a tracking camera to which visibility of the array frame is desired, or a position of the patient on an operating table.

These and other aspects, advantages and salient features of the invention will become apparent from the following detailed description, which, when taken in conjunction with the annexed drawings, where like parts are designated by like reference characters throughout the drawings, disclose embodiments of the invention.

BRIEF DESCRIPTION OF THE DRAWINGS

Aspects of the present disclosure are illustrated by way of example and are not limited by the accompanying drawings. In the drawings:

FIG. 2 illustrates the camera tracking system and the surgical robot of FIG. 1, positioned relative to a patient according to some embodiments of the present disclosure.

FIG. 4 illustrates a block diagram of a surgical system that includes an extended reality headset, a computer platform, imaging devices, and a surgical robot, which are configured to operate according to some embodiments of the present disclosure.

FIG. 8 illustrates a radiographic version angle measured relative to the coronal plane of the patient, in accordance with some embodiments of the present disclosure.

FIGS. 12A-12B provide perspective views of an array frame of a dynamic reference base in accordance with some embodiments of the present disclosure.

FIGS. 16A-16B provide perspective views of the dynamic reference base shown in FIGS. 13A-13B in the process of coupling the dynamic array to the bridge, in accordance with some embodiments of the present disclosure.

Figure 1:
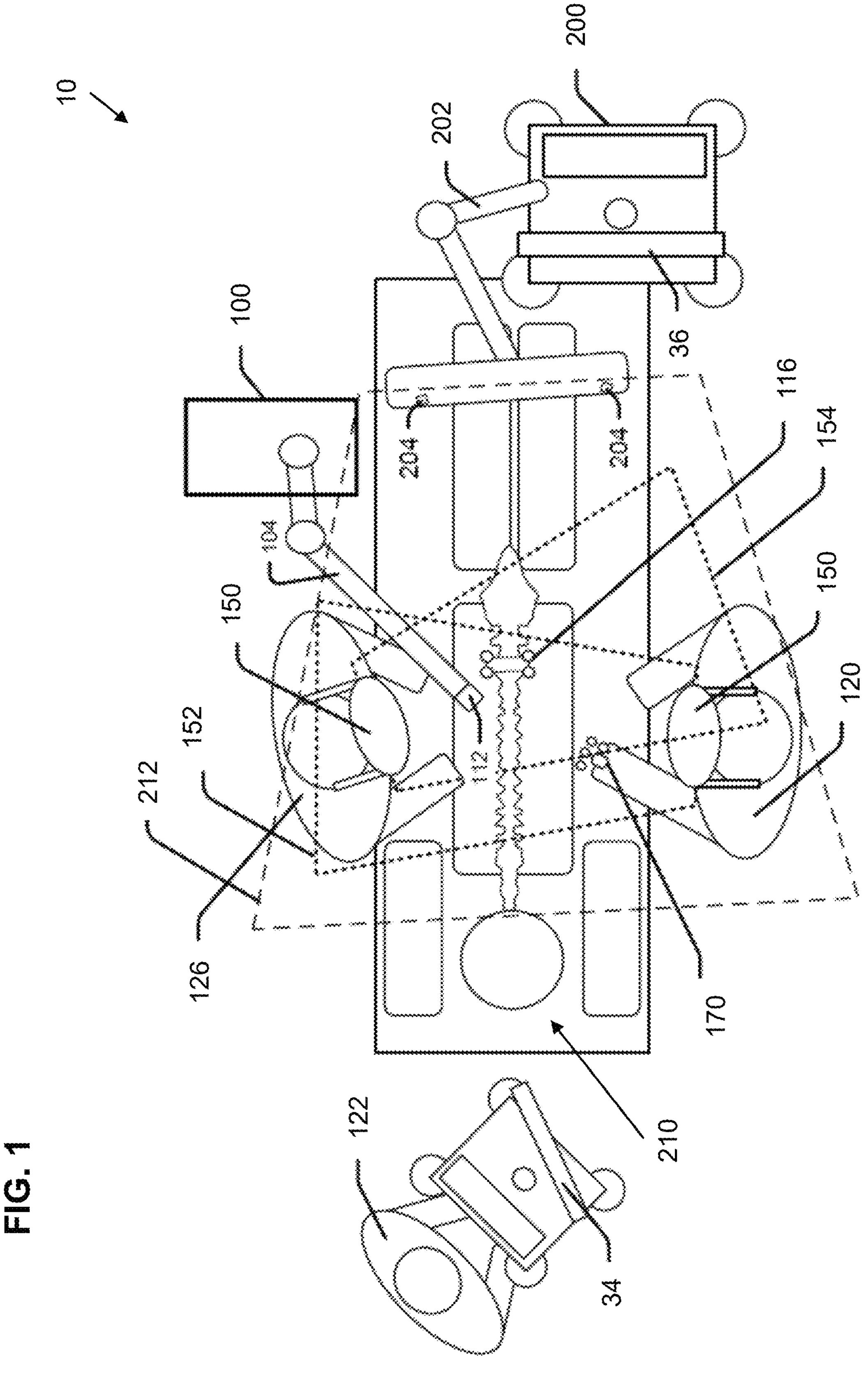
FIG. 1 is an overhead view of a surgical system arranged during a surgical procedure in a surgical room which includes a camera tracking system for computer assisted navigation during surgery, and a surgical robot for robotic assistance according to some embodiments of the present disclosure.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "attached," "supported," and "coupled" and variations thereof are used broadly and encompass both direct and indirect mountings, connections, attachments, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

The present application is related to (1) patent application Ser. No. 15/180,126, filed Jun. 13, 2016 (U.S. Pat. No. 10,842,453), (2) patent application Ser. No. 15/157,444, filed May 18, 2016 (U.S. Pub. No. 2016/0256225), and (3) patent application Ser. No. 18/743,388, filed on Jun. 14, 2024 each of which is incorporated herein by reference.

Robotic surgery systems and workflows associated therewith may provide improved outcomes in surgeries such as, e.g., THA surgeries compared to more traditional approaches. For example, robotic surgery systems may provide additional accuracy and force assistance when preparing the acetabulum, and additional accuracy and alignment when trialing and placing implants. In certain embodiments, e.g., including intra-operative CT imaging, confirmatory feedback regarding screw location may also be provided prior to drilling. Aspects of the disclosed embodiments are discussed below.

Figure 2:
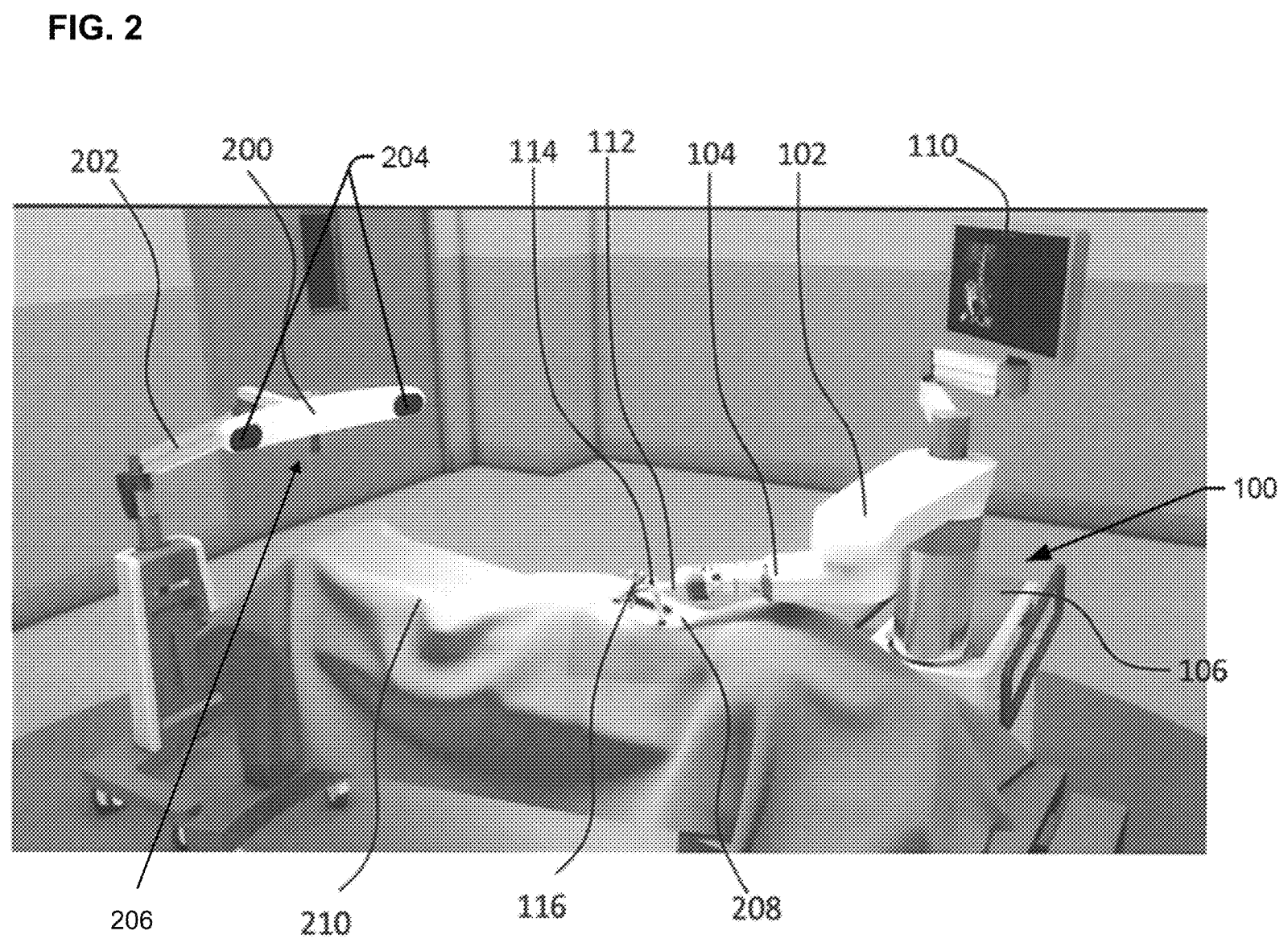
Figure 3:
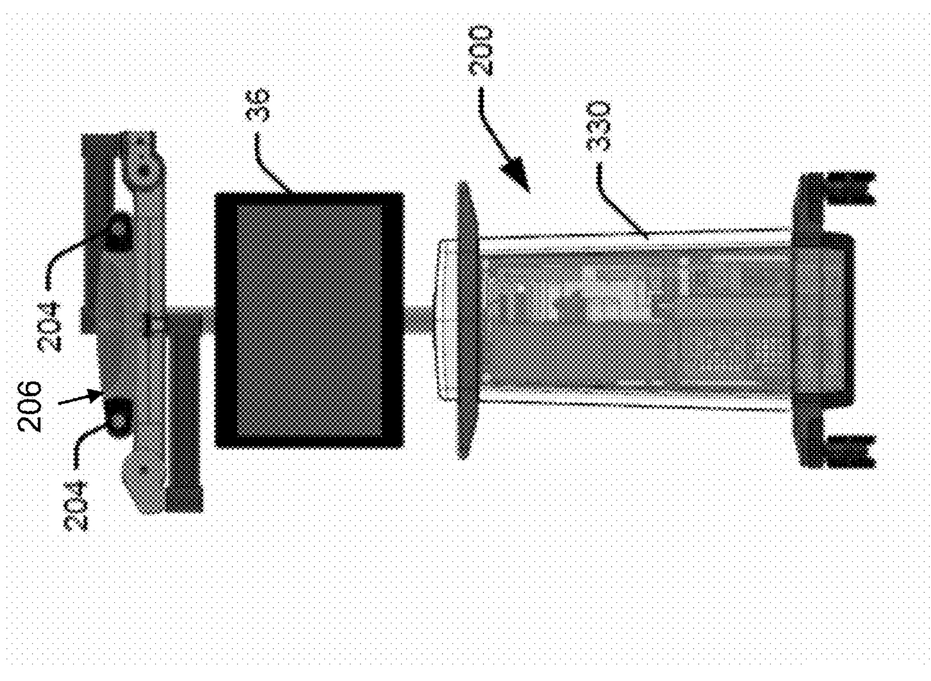
FIG. 3 further illustrates the camera tracking system and the surgical robot of FIGS. 1-2, configured according to some embodiments of the present disclosure.
Figure 3:
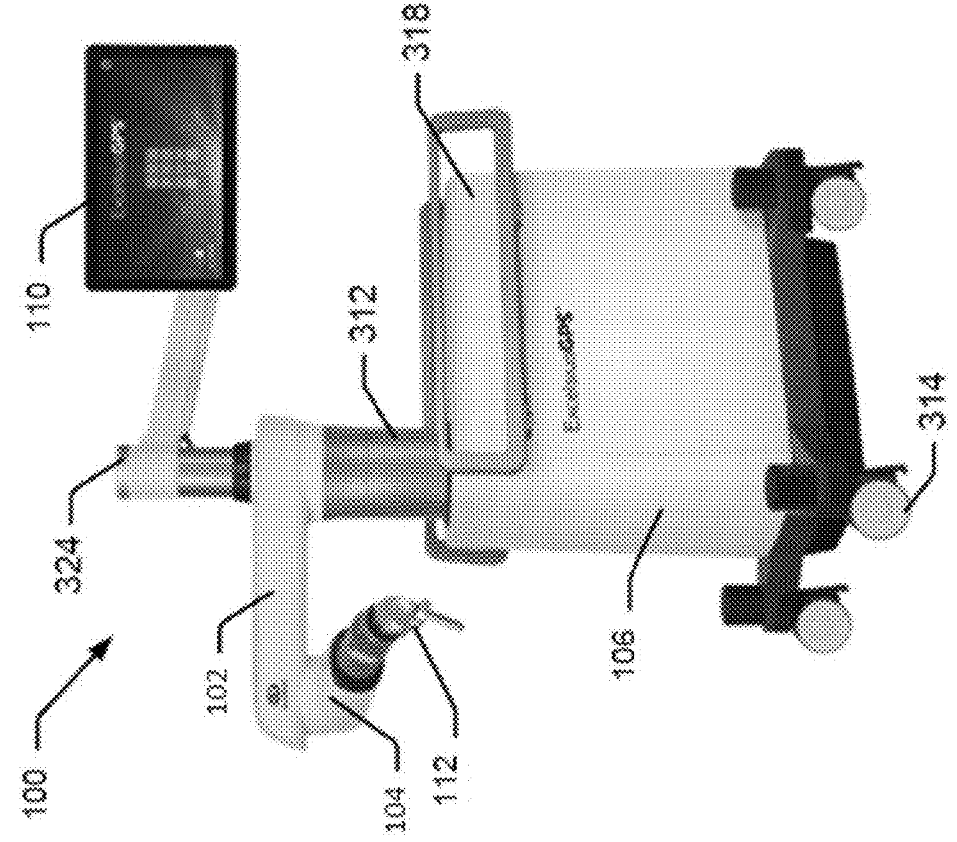

FIG. 1 is an overhead view of a surgical system 10 arranged during a surgical procedure in a surgical or operating room. The system 10 includes a camera tracking system 200 for computer assisted navigation during surgery and may further include a surgical robot 100 for robotic assistance according to some embodiments. FIG. 2 illustrates the camera tracking system 200 and the surgical robot 100 positioned relative to a patient according to some embodiments. FIG. 3 further illustrates the camera tracking system 200 and the surgical robot 100 configured according to some embodiments. FIG. 4 illustrates a block diagram of a surgical system 10 that includes an extended reality (XR) headset 150, a computer platform 400, imaging devices 420, and the surgical robot 100 which are configured to operate according to some embodiments.

The camera tracking system 200 (FIGS. 1-4) in some cases includes an intraoperative imaging system, that can include distinct imaging modalities. These imaging modalities may include one or more of fluoroscopy, 2D Radiography, and Cone-beam computed tomography (CBCT). Fluoroscopy is a medical imaging technique that shows a continuous X-ray image on a monitor, much like an X-ray movie. 2D Radiography is an imaging technique that uses X-rays to view the internal structure of a non-uniformly composed and opaque object such as the human body. CBCT (or, cone beam 3D imaging or C-arm CT), is a medical imaging technique consisting of X-ray computed tomography where the X-rays are divergent, forming a cone. The camera tracking system 200 is capable of: (1) capturing 3-Dimensional (3D) images (e.g., CT, CBCT, MCT, PET, Angiogram, MRI, ultrasound, etc.), (2) capturing 2-Dimensional (2D) images (e.g., fluoroscopy, digital radiography, ultrasound, etc.), and (3) containing an integrated or detachable navigation array having tracking markers (e.g., NIR retroreflective, NIR LED, visible, etc.), which is calibrated to the image space of the 2D and 3D images.

The surgical robot 100 is capable of: (1) using registered 2D and/or 3D images for surgical planning, navigation, and guidance in a variety of workflows (e.g., intraoperative 3D, intraoperative 2D, preoperative 3D to 2D, and intraoperative 3D to 2D, etc.); and (2) containing a camera tracking system 200 capable of tracking markers (e.g., NIR retroreflective, NIR LED, visible, etc.). In some cases, as noted herein, a dynamic reference base (DRB) (or patient reference array) 116 is (1) capable of rigidly attaching to the patient anatomy, and (2) contains an array of tracking markers (e.g., NIR retroreflective, NIR LED, visible, etc.).

The XR headsets 150 may be configured to augment a real-world scene with computer generated XR images while worn by personnel in the operating room. The XR headsets 150 may be configured to provide an augmented reality (AR) viewing environment by displaying the computer generated XR images on a see-through display screen that allows light from the real-world scene to pass therethrough for combined viewing by the user. Alternatively, the XR headsets 150 may be configured to provide a virtual reality (VR) viewing environment by preventing or substantially preventing light from the real-world scene from being directly viewed by the user while the user is viewing the computer-generated AR images on a display screen. The XR headsets 150 can be configured to provide both AR and VR viewing environments. Thus, the term XR headset encompasses both or either of an AR headset or a VR headset.

With continuing reference to FIGS. 1-4, the surgical robot 100 may include, for example, one or more robot arms 102, 104, a display 110, an end effector 112, for example including a guide tube, and an end effector reference element 114 which can include one or more tracking fiducials. A patient reference element (or DRB) 116 (shown in FIG. 1) has a plurality of tracking fiducials and is secured directly to the patient 210. For example, a navigated pelvis DRB marker array may be placed intra-incision or extra-incision with the help of cortical pins drilled into the pelvic bone. In some embodiments, the DRB is oriented to be visible by the tracking camera(s) 204 (e.g., a stereoscopic tracking camera) installed on the camera tracking system 200 and/or the XR headset 150. A reference element 170 is attached to or formed on an instrument, surgical tool, surgical implant device, etc.

The camera tracking system 200 includes tracking cameras 204 which may be spaced apart to provide stereo cameras configured with partially overlapping fields-of-view. The camera tracking system 200 can have any suitable configuration of arm(s) 202 to move, orient, and support the tracking cameras 204 in a desired location, and may contain at least one processor operable to track the location of an individual fiducial and pose of an array of fiducials of a reference element.

As used herein, the term "pose" refers to the location (e.g., along three orthogonal axes, e.g., the x-, y-, and z-axes) and/or the rotation angle (e.g., about the three orthogonal axes) of fiducials (e.g., DRB) relative to another fiducial (e.g., surveillance fiducial) and/or to a defined coordinate system (e.g., camera coordinate system, navigation coordinate system, etc.). A pose may therefore be defined based on only the multidimensional location of the fiducials relative to another fiducial and/or relative to the defined coordinate system, based on only the multidimensional rotational angles of the fiducials relative to the other fiducial and/or to the defined coordinate system, or based on a combination of the multidimensional location and the multidimensional rotational angles. The term "pose" therefore is used to refer to location, rotational angle, or combination thereof of, e.g., an instrument reference element 170, a patient reference element 116, or the like.

The tracking cameras 204 may include, e.g., infrared cameras (e.g., bifocal or stereophotogrammetric cameras) operable to identify, for example, active and passive tracking fiducials for single fiducials (e.g., a surveillance fiducial) and reference elements which can be formed on or attached to the patient 210 (e.g., patient reference element or DRB 116), end effector 112 (e.g., end effector reference element 114), XR headset(s) 150 worn by a surgeon 120 and/or a surgical assistant 126, etc. in a given measurement volume of a camera coordinate system while viewable from the perspective of the tracking cameras 204. The tracking cameras 204 may scan the given measurement volume and detect light that is emitted or reflected from the fiducials in order to identify and determine locations of individual fiducials and poses of the reference elements in three-dimensions. For example, active reference elements may include infrared-emitting fiducials that are activated by an electrical signal (e.g., infrared light emitting diodes (LEDs)), and passive reference elements may include retro-reflective fiducials that reflect infrared light (e.g., they reflect incoming IR radiation into the direction of the incoming light), for example, emitted by illuminators on the tracking cameras 204 or other suitable device.

The XR headsets 150 may each include tracking cameras (e.g., spaced apart stereo cameras) that can track the location of a surveillance fiducial and poses of reference elements within the XR camera headset fields of view (FOVs) 152 and 154, respectively. Accordingly, as illustrated in FIG. 1, the location of the surveillance fiducial and the poses of reference elements on various objects such as, e.g., instrument reference element 170 and patient reference element 116, can be tracked while in the FOVs 152 and 154 of the XR headsets 150 and/or a FOV 212 of the tracking cameras 204.

FIGS. 1 and 2 illustrate a potential configuration for the placement of the camera tracking system 200 and the surgical robot 100 in an operating room environment. Computer assisted navigated robotic surgery can be provided by the surgical robot 100, the camera tracking system 200 controlling the XR headsets 150 and/or other displays 34, 36, and 110 to display surgical procedure navigation information.

The camera tracking system 200 may operate using tracking information and other information provided by multiple XR headsets 150 such as inertial tracking information and optical tracking information (frames of tracking data). The XR headsets 150 operate to display visual information and may play-out audio information to the wearer. This information can be from local sources (e.g., the surgical robot 100), imaging devices 420 (FIG. 4), remote sources (e.g., patient medical image database), and/or other electronic equipment. The camera tracking system 200 may track fiducials in 6 degrees-of-freedom (6 DOF) relative to three axes of a 3D coordinate system and rotational angles about each axis. The XR headsets 150 may also operate to track hand poses and gestures to enable gesture-based interactions with "virtual" buttons and interfaces displayed through the XR headsets 150, and can also interpret hand or finger pointing or gesturing as various defined commands. Additionally, the XR headsets 150 may have a 1-10× magnification digital color camera sensor called a digital loupe. In some embodiments, one or more of the XR headsets 150 are minimalistic XR headsets that display local or remote information but include fewer sensors and are therefore more lightweight.

An "outside-in" machine vision navigation bar 206 supports the tracking cameras 204 and may include a color camera. The machine vision navigation bar generally has a more stable view of the environment because it does not move as often or as quickly as the XR headsets 150 while positioned on wearers' heads. The patient reference element (or, DRB) 116 is generally rigidly attached to the patient 210 with stable pitch and roll relative to gravity. This local rigid patient reference 116 can serve as a common reference for reference frames relative to other tracked elements, such as a reference element 114 on the end effector 112, instrument reference element 170, and reference elements on the XR headsets 150.

In some embodiments, at the end of the end effector 112, instruments are connected to perform operations such as resection, reaming, and implant placement.

The surgical robot 100 may be positioned near or next to patient 210 as shown in FIGS. 1-2. The robot 100 can be positioned at any suitable location near the patient 210 depending on the area of the patient 210 undergoing the surgical procedure. The camera tracking system 200 may be separate from the robot system 100 and positioned at the foot of patient 210. This location allows the tracking camera 200 to have a direct visual line of sight to the surgical area 208, e.g., the hip area (FIG. 2). In the configuration shown in FIG. 1, the surgeon 120 may be positioned across from the robot 100, but is still able to manipulate the end effector 112 and the display 110. A surgical assistant 126 may be positioned across from the surgeon 120 again with access to both the end effector 112 and the display 110. If desired, the locations of the surgeon 120 and the assistant 126 may be reversed. An anesthesiologist 122, nurse, or scrub tech can operate equipment which may be connected to display information from the camera tracking system 200 on a display 34 (FIG. 1).

With respect to the other components of the robot 100, the display 110 can be attached to the surgical robot 100 or in a remote location. The end-effector 112 may be coupled to the robot arm 104 and be controlled by at least one motor. An upper arm 102 may further couple the arm 104 to the column 312 of the robot 100. In some embodiments, end effector 112 includes a guide tube, which is configured to receive and orient a surgical instrument, tool, or implant used to perform a surgical procedure on the patient 210. For example, the end effector 112 is adapted to receive a surgical instrument or a portion thereof, to removably couple to the instrument, and to manipulate the instrument such as by translating and rotating the instrument. In some other embodiments, the end-effector 112 includes a passive structure guiding a saw blade (e.g., sagittal saw) along a defined cutting plane.

As used herein, the term "end effector" is used interchangeably with the terms "end effectuator" and "effectuator element." The term "instrument" is used in a non-limiting manner and can be used interchangeably with "tool" and "implant" to generally refer to any type of device that can be used during a surgical procedure in accordance with embodiments disclosed herein. The more general term, device, can also refer to structure of the end effector, etc. Example instruments, tools, and implants include, without limitation, reamer constructs, drills, screwdrivers, saws, dilators, retractors, probes, implant inserters, and implant devices such as shells and trial shells, screws, spacers, interbody fusion devices, plates, rods, etc. Although generally shown with a guide tube, it will be appreciated that the end-effector 112 may be replaced with any suitable instrumentation for use in surgery. In some embodiments, end-effector 112 can comprise any known structure for effecting the movement of the surgical instrument in a desired manner.

The surgical robot 100 is operable to control the translation and orientation of the end-effector 112. The robot 100 may move the end-effector 112 under computer control along x-, y-, and z-axes, for example. The end-effector 112 can be configured for selective rotation about one or more of the x-, y-, and z-axes, and a Z Frame axis, such that one or more of the Euler Angles (e.g., roll, pitch, and/or yaw) associated with the end effector 112 can be selectively computer controlled. In some embodiments, selective control of the translation and orientation of end effector 112 and associated surgical instrument can permit performance of medical procedures with significantly improved accuracy compared to conventional robots that utilize, for example, a 6 DOF robot arm comprising only rotational axes. For example, the surgical robot 100 may be used to operate on patient 210, and robot arm 104 can be positioned above the body of patient 210, with end-effector 112 selectively angled relative to the z-axis toward the body of patient 210.

In some example embodiments, the XR headset(s) 150 can be controlled to dynamically display an updated graphical indication of the pose of the surgical instrument so that the user, e.g., surgeon 120, can be aware of the pose of the surgical instrument at all times during the procedure.

In some further embodiments, surgical robot 100 can be operable to correct the path of a surgical instrument guided by the robot arm 104 if the surgical instrument strays from the selected, preplanned, or defined trajectory. The surgical robot 100 can be operable to permit stoppage, modification, and/or manual control of the movement of end effector 112 and/or the surgical instrument. Thus, in use, a surgeon 120 or other user can use the surgical robot 100 as part of computer assisted navigated surgery, and has the option to stop, modify, or manually control the autonomous or semi-autonomous movement of the end-effector 112 and/or the surgical instrument.

Fiducials of reference elements can be formed on or connected to robot arms 102 and/or 104, the end effector 112 (e.g., end effector element 114 in FIG. 2), and/or a surgical instrument (e.g., instrument element 170) to enable tracking of poses in a defined coordinate system, e.g., such as in six degrees of freedom (DOF) along three orthogonal axes and rotation about the axes. The reference elements 114, 116, 170 enable each of the marked objects (e.g., the end-effector 112, the patient 210, and the surgical instruments, respectively) to be tracked by the tracking camera 200, and the tracked poses can be used to provide navigated guidance during a surgical procedure and/or to control movement of the surgical robot 100 for guiding the end effector 112 and/or an instrument manipulated by the end effector 112. The instrument manipulated by the end effector 112 may include, e.g., a reamer 124 or an inserter adapted to insert an implant.

Referring to FIG. 3 the surgical robot 100 may include a display 110, upper arm 102, lower arm 104, end effector 112, vertical column 312, casters 314, a table 318, and ring 324 which uses lights to indicate statuses and other information. Cabinet 106 may house electrical components of surgical robot 100 including, but not limited to, a battery, a power distribution module, a platform interface board module, and a computer. The camera tracking system 200 may include a display 36, tracking cameras 204, arm(s) 202 (FIG. 1), a computer housed in cabinet 330, and other components.

In computer assisted navigated surgeries, perpendicular 2D scan slices, such as axial, sagittal, and/or coronal views of patient anatomical structure are displayed to enable user visualization of the patient's anatomy alongside the relative poses of surgical instruments. An XR headset or other display can be controlled to display one or more 2D scan slices of patient anatomy along with a 3D graphical model of anatomy. The 3D graphical model may be generated from a 3D scan of the patient, e.g., by a CT scan device, and/or may be generated based on a baseline model of anatomy which isn't necessarily formed from a scan of the patient.

Example Surgical System

FIG. 4 illustrates a block diagram of a surgical system 10 that includes a surgical robot 100, a computer platform 400 including, inter alia, the camera tracking system 200, imaging device(s) 420, and XR headset(s) 150 which are configured to operate as described herein, according to some embodiments.

The imaging device(s) 420 may include a C-arm imaging device, an O-arm imaging device, other imaging device, and/or a patient image database of 2D and/or 3D images. The XR headset 150 provides a human interface for performing navigated surgical procedures. The XR headset 150 can be configured to provide functionalities, e.g., via the computer platform 400, that include without limitation any one or more of: identification of hand gesture-based commands, and display of XR graphical objects on a display device 438 of the XR headset 150 and/or another display device. The display device 438 may include a video projector, flat panel display, etc. The user may view the XR graphical objects as an overlay anchored to particular real-world objects viewed through a see-through display screen. The XR headset 150 may additionally or alternatively be configured to display on the display device 438 video streams from cameras mounted to one or more XR headsets 150 and other cameras.

Electrical components of the XR headset 150 can include a plurality of cameras 430, a microphone 432, a gesture sensor 434, a pose sensor (e.g., inertial measurement unit (IMU)) 436, the display device 438, and a wireless/wired communication interface 440. The cameras 430 of the XR headset 150 may be visible light capturing cameras, near infrared capturing cameras, or a combination of both.

The cameras 430 may be configured to operate as the gesture sensor 434 by tracking for identification user hand gestures performed within the field-of-view of the camera(s) 430. Alternatively, the gesture sensor 434 may be a proximity sensor and/or a touch sensor that senses hand gestures performed proximately to the gesture sensor 434 and/or senses physical contact, e.g., tapping on the sensor 434 or its enclosure. The pose sensor 436, e.g., IMU, may include a multi-axis accelerometer, a tilt sensor, and/or another sensor that can sense rotation and/or acceleration of the XR headset 150 along one or more defined coordinate axes. Some or all of these electrical components may be contained in a head-worn component enclosure or may be contained in another enclosure configured to be worn elsewhere, such as on the hip or shoulder.

As explained above, the surgical system 10 includes the camera tracking system 200 which may be connected to a computer platform 400 for operational processing and which may provide other operational functionality including a navigation controller 404 and/or an XR headset controller 410. The surgical system 10 may further include the surgical robot 100. The navigation controller 404 can be configured to provide visual navigation guidance to an operator for moving and positioning a surgical tool relative to patient anatomical structure based on a surgical plan, e.g., from a surgical planning function, defining where a surgical procedure is to be performed using the surgical tool on the anatomical structure and based on a pose of the anatomical structure determined by the camera tracking system 200. The navigation controller 404 may be further configured to generate navigation information based on a target pose for a surgical tool, a pose of the anatomical structure, and a pose of the surgical tool and/or an end effector 112 of the surgical robot 100. The navigation information may be displayed through the display device 438 of the XR headset 150 and/or another display device to indicate where the surgical tool and/or the end effector 112 of the surgical robot 100 should be moved to perform a surgical procedure according to a defined surgical plan.

The electrical components of the XR headset 150 can be operatively connected to the electrical components of the computer platform 400 through the wired/wireless interface 440. The electrical components of the XR headset 150 may be operatively connected, e.g., through the computer platform 400 or directly connected, to various imaging devices 420, e.g., the C-arm imaging device, the O-arm imaging device, other imaging device(s), the patient image database, and/or to other medical equipment through the wired/wireless interface 440.

The surgical system 10 may include a XR headset controller 410 that at least partially resides in the XR headset 150, the computer platform 400, and/or another system component connected via wired cables and/or wireless communication links. Various functionality may be provided by software executed by the XR headset controller 410. The XR headset controller 410 is configured to receive information from the camera tracking system 200 and the navigation controller 404, and to generate an XR image based on the information for display on the display device 438.

The XR headset controller 410 can be configured to operationally process frames of tracking data from the cameras 430 (tracking cameras), signals from the microphone 432, and/or information from the pose sensor 436 and the gesture sensor 434, to generate information for display as XR images on the display device 438 and/or for display on other display devices for user viewing. Thus, the XR headset controller 410 as illustrated as a circuit block within the XR headset 150 is to be understood as being operationally connected to other illustrated components of the XR headset 150 but not necessarily residing within a common housing or being otherwise transportable by the user. For example, the XR headset controller 410 may additionally or alternatively reside within the computer platform 400 which, in turn, may reside within the cabinet 330 of the camera tracking system 200, the cabinet 106 of the surgical robot 100, etc.

Exemplary Patient Registration Workflows

In some embodiments of the present disclosure, the system 10, e.g., computer platform 400, may perform one of a number of available workflows to register a patient to the surgical system 10 prior to surgery. The workflows may further include isolating a target area for the surgical procedure from non-target surgical areas. In one example, the target surgical area may include the acetabulum, and the non-target surgical area may include the femur.

In one embodiment, the workflow may be an imageless workflow in which no pre-operative images are used. Instead, information about the patient anatomy in the operating room (OR) can be obtained by the surgeon measuring key parameters of the patient's bone using the system as described herein. For example, the computer platform 400 of the system 10 operates to identify the locations of landmarks (e.g., points, axes, and/or surfaces) on the bone and register the locations either concurrently with the identification or thereafter. The locations can be used to define reference plane(s) (e.g., anterior pelvic plane (APP) and/or functional pelvic plane (FPP)) which, in turn, are used to plan implants and navigate the robot and surgical instruments for THA surgical procedures.

In some embodiments, the only pre-operative use case associated with the imageless workflow may be the initial patient assessment. The surgeon may assess the patient's mobility and health status with assistance from sensors (e.g., sensors made by Globus Medical which are attached to the leg), physical exercises, and/or clinical surveys to determine if THA is recommended. Gathered data may then be stored and processed by the system before being analyzed by the surgeon to facilitate a final decision. Subsequently, the data may be reused by an application (e.g., surgery planning application by Globus Medical) to establish the most appropriate implant surgical plan.

Figure 5:
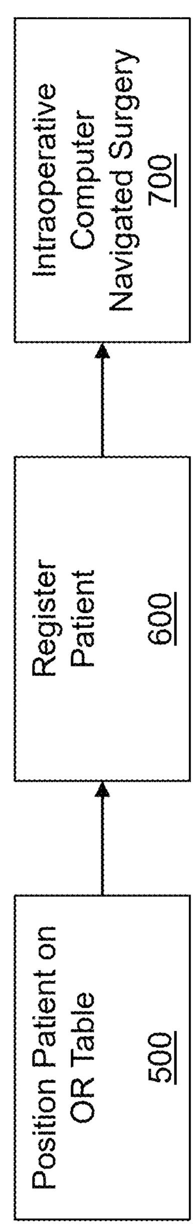
FIG. 5 illustrates a flowchart of a workflow during an intra-operative portion of a total hip arthroplasty (THA) surgery, in accordance with some embodiments of the present disclosure.

FIG. 5 illustrates a flowchart for an imageless workflow during an intra-operative portion of a THA surgery, in accordance with some embodiments of the present disclosure. In some embodiments, after positioning the patient on the operating room table (process 500), some of the operations discussed above and below may be performed during process 600 to register a patient and before another process 700 for intraoperative computer navigated surgery. In the case of a hip, a pelvis or acetabulum of the patient is registered in the tracking coordinate system of the camera tracking system 200. As shown in FIG. 1, the pelvis or acetabulum is registered in the optical coordinate system. In one embodiment, the registration is done in an imageless modality without the use of any medical images such as X-rays or CT images from an imaging device. As noted herein, in other embodiments, registration is performed using one or more pre-operative X-ray images and/or CT images.

Figure 6:
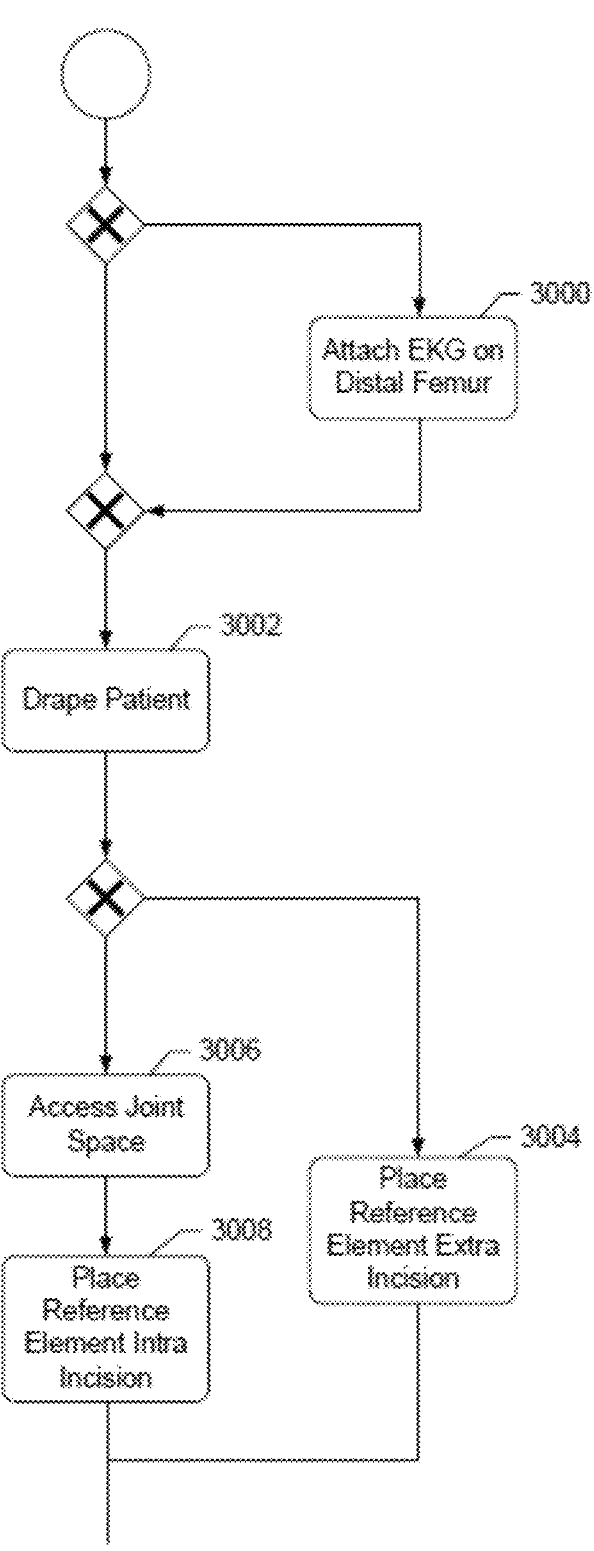
FIG. 6 illustrates a flowchart of a patient preparation process before registration, in accordance with some embodiments of the present disclosure.

FIG. 6 illustrates a flowchart of a patient preparation process before registration, in accordance with some embodiments of the present disclosure.

The patient preparation process may begin with a patient being positioned in a lateral or supine position on the OR table. The patient's body is prepared for registration. Optionally, in process 3000, an EKG/ECG patch electrode is attached on or adjacent a distal end of the patient's femur. The EKG/ECG patch electrode may be placed on the center of the patella or slightly inferior to the center. In some embodiments, the patch location is in line with the anatomic axis of the femur. This patch may be used to acquire the most distal point of the femur under the drape at a later stage. This patch may also be used to track the femur in space (e.g., when the patient's leg is moved during surgery) and may also be used to assist in measuring the patient's leg length. However, in some embodiments, this operation (process 3000) is skipped.

In some embodiments, the EKG/ECG patch electrode includes an adhesive patch that is removably attachable to the patient. In some embodiments, the patch may be black or dark to be more visible to the tracking camera. In other embodiments, the patch and patch electrodes are not visible by the tracking camera as they are under a drape. The patch geometry (like a nipple) will help the surgeon to always touch a single point on or adjacent the distal part of the femur (anterior patella region) with a navigated stylus/instrument which is trackable by the tracking camera. This ensures that the surgeon always collects the same point to measure the leg length or medio-lateral offset.

In process 3002, the patient body is draped. Then, depending on the surgeon's technique, the navigated pelvis DRB is placed intra-incision (processes 3006-3008) or extra-incision (process 3004) with the help of cortical pins drilled into the pelvic bone. In some embodiments, the DRB is oriented to be visible to the tracking camera(s), e.g., a stereoscopic tracking camera installed on the camera tracking system 200 (FIG. 1) or the XR headset 150 (FIG. 1). In one embodiment, the operation to place the DRB intra-incision, includes using the system to track and navigate access to the joint space (process 3006) and placing the reference element intra-incision. In an alternative embodiment, the reference element is placed extra-incision (process 3004) and the system does not necessarily need to be used to track and navigate access to the joint space.

After the reference element or DRB 116 has been placed intra-incision or extra-incision, data points and axes can be collected on the patient anatomy with the assistance of navigated instruments and using the pelvis DRB coordinate system as a spatial reference. In addition to this, two pelvic reference planes can be established to plan placement of implants by measuring angular deviations such as inclination and version of the acetabular cup implant as shown in FIGS. 7-8.

Figure 7:
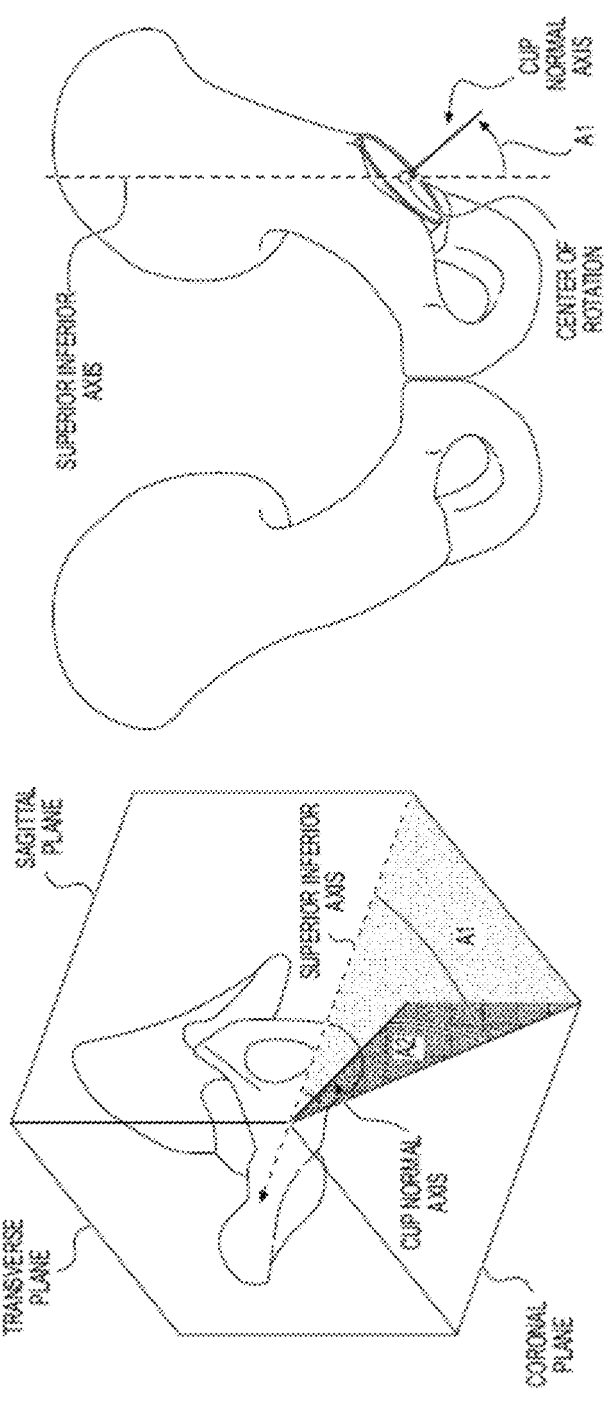
FIG. 7 illustrates a radiographic inclination angle measured in the coronal plane of the patient, in accordance with some embodiments of the present disclosure.
Figure 8:
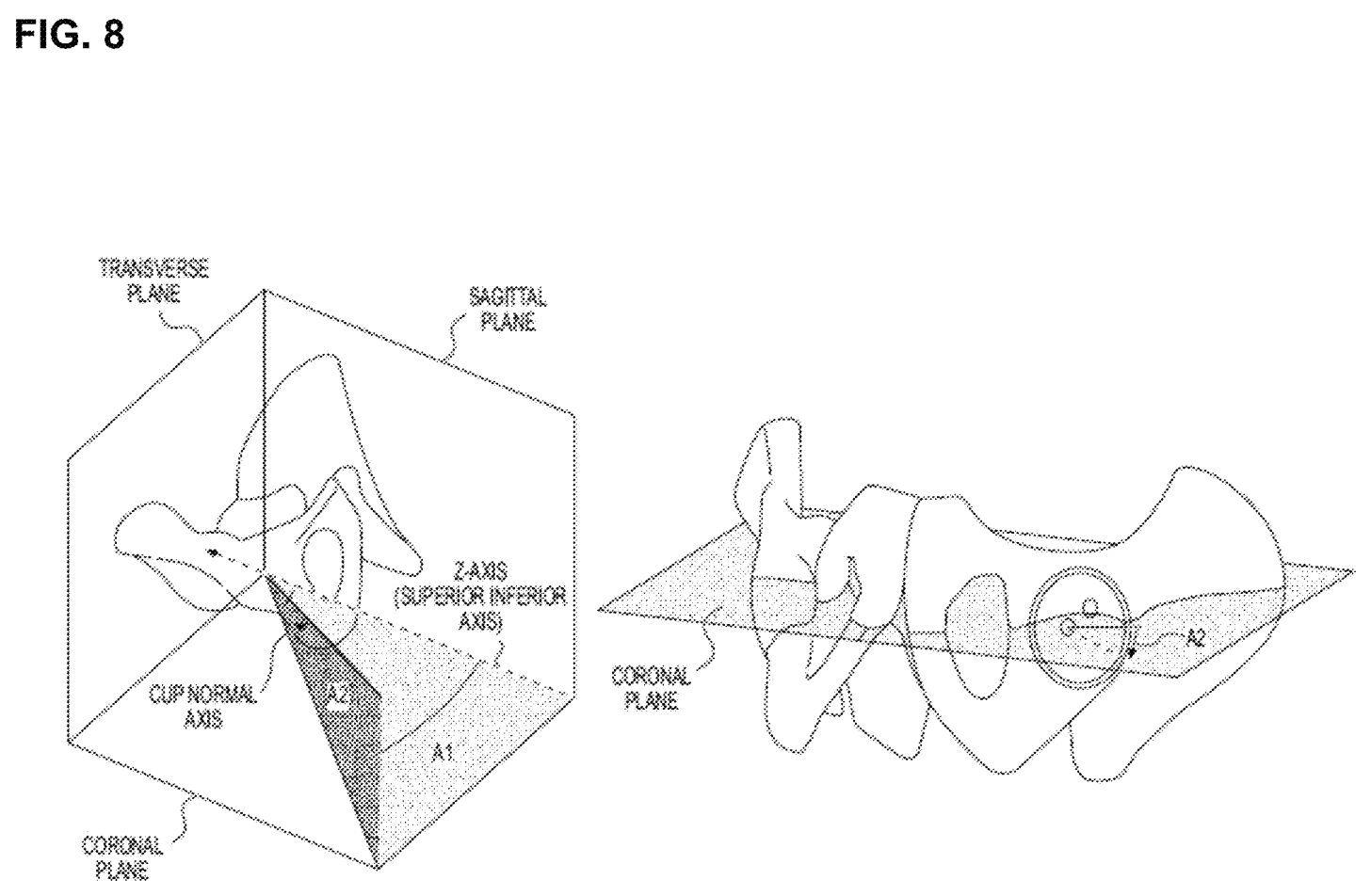

FIG. 7 illustrates a radiographic inclination angle measured in the coronal plane of the patient, in accordance with some embodiments of the present disclosure. In some embodiments, the surgeon may use a navigated instrument to palpate or paint the surface of the acetabular cavity of the patient to determine a center of rotation of the acetabulum. FIG. 8 illustrates a radiographic version angle measured relative to the coronal plane of the patient, in accordance with some embodiments of the present disclosure. The two pelvic reference planes (or coronal or frontal planes), the anterior pelvic plane (APP) and functional pelvic plane (FPP), are determined or defined using different landmarks and axes as shown on FIG. 9 and described in further detail below.

It is to be understood herein that although the user interfaces and associated operations are described as being performed in a certain sequence, they may be performed in other sequences while still being within disclosed embodiments. Moreover, it is not necessary that all of the user interfaces and/or described operations be performed. Instead, fewer operations may be performed while still being within disclosed embodiments. Further, additional registration approaches can include image-based and imageless workflows. Combinations of these registration approaches are also possible in keeping with the various disclosed embodiments.

Figure 9:
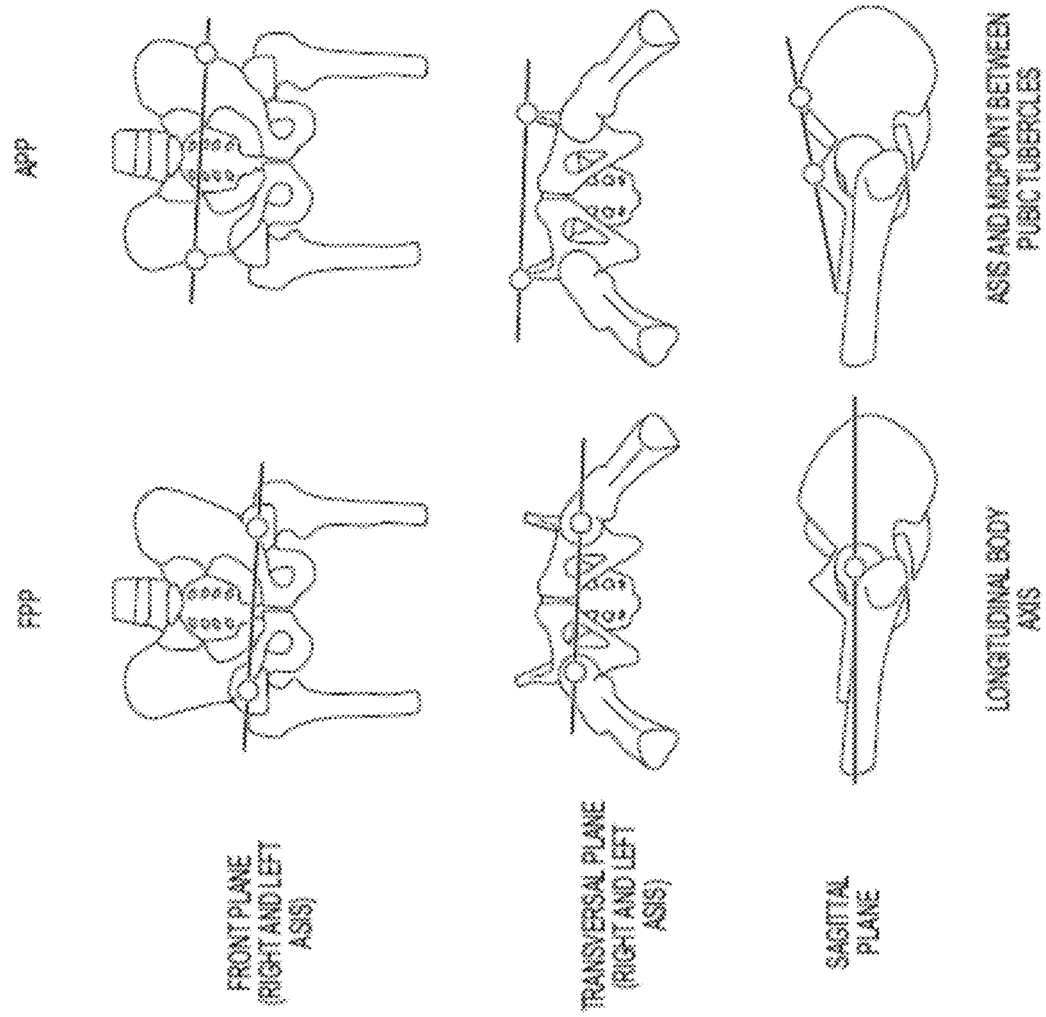
FIG. 9 illustrates different views of landmarks and axes for registration of a functional pelvic plane (FPP) and an anterior pelvic plane (APP) of a patient, in accordance with some embodiments of the present disclosure.
Figure 10B:
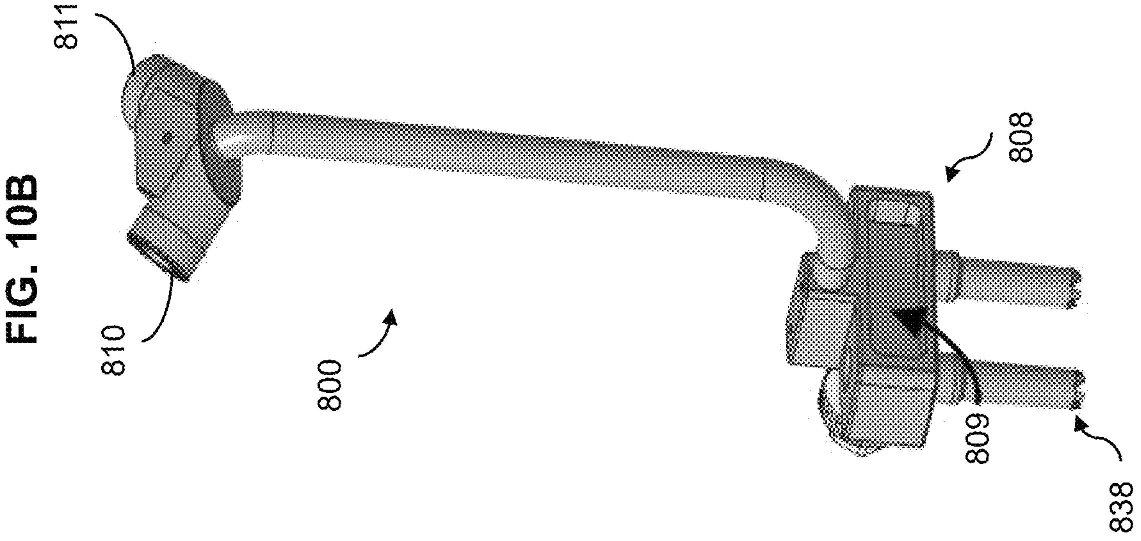
FIGS. 10A-10B provide perspective views of a bridge element of a dynamic reference base in accordance with some embodiments of the present disclosure.
Figure 10A:
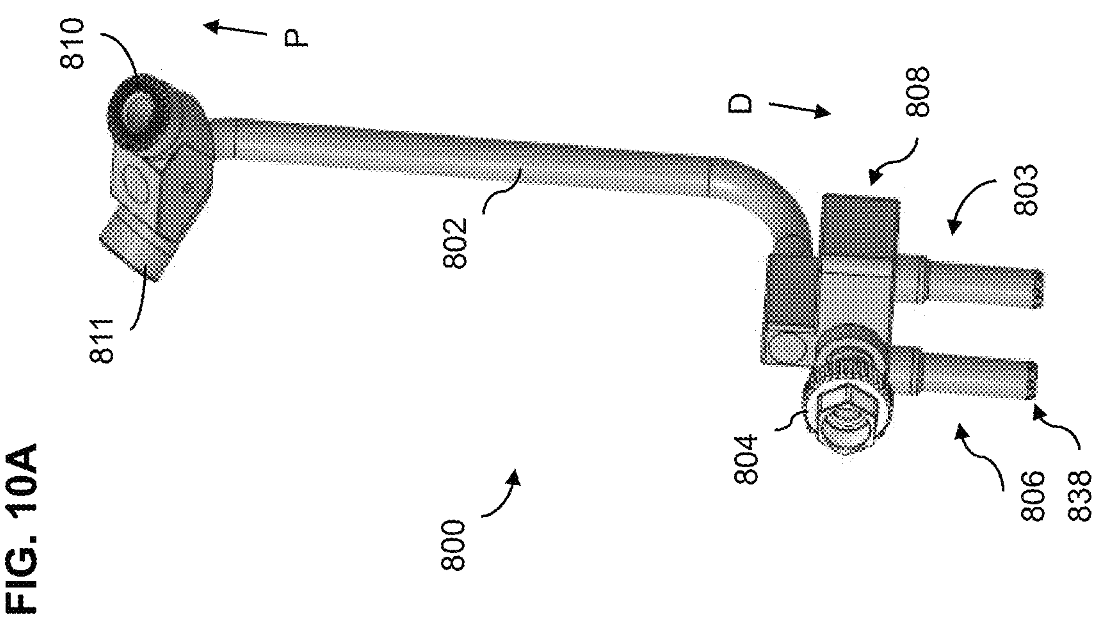

During a patient registration procedure, landmarks used to register patient anatomy can be extracted using either single point palpation collection or surface painting (resulting in a point cloud of locations). FIG. 9 illustrates different views of landmarks and axes for registration of the FPP and APP of a patient, in accordance with some embodiments of the present disclosure. The landmarks and axes used to register the APP and FPP planes are described in more detail in U.S.

patent application Ser. No. 18/430,077, filed Feb. 1, 2024, previously incorporated by reference herein.

Further, U.S. patent application Ser. No. 18/430,077 discloses processes for registration of a pelvic acetabulum of a patient (including painting the acetabular cavity), in accordance with various embodiments of the present disclosure. For example, to define the APP and FPP origins, the pelvic acetabular center of rotation can be determined after removing the femoral head of the patient from the acetabular cavity. The acetabular cavity may be made accessible by cutting the femoral neck and by removing the femoral head from the acetabular cavity. In some embodiments, a cork screw instrument may be used to remove the femoral head from the acetabular cavity.

The surface of the acetabular cavity can then be painted using the navigated instrument (e.g., a stylus). For example, the surgeon may use the navigated instrument (e.g., stylus) to palpate the surface of the acetabular cavity, as the tracking camera measures the position of a ball on the end of the stylus in a continuous way. This process provides a cloud of points for the measured positions (locations). At the same time, the tracking camera may also monitor and track the pose of the patient DRB 116 attached to the pelvis such that the pose of the stylus can be tracked relative to the pose of the patient DRB. Alternatively, the surgeon may subsequently measure a predefined number or percentage of points by palpating them one-by-one. Based on these points and the tracking data of the stylus and patient DRB 116, the center of rotation of the pelvic acetabular cavity is determined. Additionally, based on these points, the surface of the acetabular cavity may be registered in the system and/or a 3D model may be generated or modified based on these points. Next, the acetabular cavity shape can be recreated (e.g., in a 3D model) by the system based on the measured cloud of points and using other algorithms, e.g., for outlier removals and surface fitting.

While certain imageless approaches are described herein and in U.S. patent application Ser. No. 18/430,077, previously incorporated by reference herein, other example methods of performing imageless and image-based registration of the pelvis to the tracking coordinate system of the tracking system (e.g. optical coordinate system). These methods may also be used to, e.g., determine a native center of rotation of the acetabulum, derive or define an FPP, and derive or define an APP. Registration may allow a navigation system or robotic system to track any navigated instrument or end effector 112 or any tool attached to the end effector 112 relative to the pelvis as tracked by a patient dynamic reference base 116 attached to the pelvis. Various registration methods described herein can be combined in keeping with various disclosed embodiments.

For example, in one imageless method, an APP is derived by either touching various known points (e.g., left and right anterior superior iliac spine (ASIS) and pubic symphysis) with a navigated instrument, or by a physician lining up a plane or axis defined by the navigated instrument along or parallel to the APP. With the center of rotation and APP determined, the system (either a navigation system or a combined navigation and robot system 100) has sufficient information to register the acetabulum in the coordinate system (e.g., optical coordinate system) of the camera tracking system 200. In both of the above-noted example methods, the tracking system may be constantly monitoring and tracking the pose of the patient DRB 116 attached to the pelvis while also tracking the navigated instrument (e.g., stylus) such that the pose of the instrument can be tracked relative to the pose of the patient DRB, at least for purposes of registering the pelvis relative to the patient DRB 116 in the tracking coordinate system of the camera tracking system 200.

Some exemplary image-based examples include the use of pre-operative CT images. In one such exemplary image-based approach to patient registration, pre-operative CT and intra-operative fluoroscopy images are merged, the non-target surgical area is excluded, and the location of the target surgical area is registered based on the merged CT image and fluoroscopy image, as described in patent application Ser. No. 18/743,388, filed on Jun. 14, 2024, incorporated herein by reference. The same application also describes another exemplary image-based approach to patient registration, pre-operative CT and intra-operative point cloud data acquired via a navigated instrument are merged, and the location of the target surgical area is registered based on the merged CT image and point cloud data.

Also, the same application (application Ser. No. 18/743,388) describes an image-based registration approaches without first obtaining pre-operative CT images. In one such exemplary approach to patient registration, intra-operative fluoroscopy images are obtained, and an APP and FPP are identified. The FPP images and APP images are merged, excluding the non-target surgical area, and the location of the target surgical area is registered based on the merged APP and FPP fluoroscopy images.

In a further exemplary image-based approach to patient registration, intra-operative fluoroscopy images are obtained, and intra-operative point cloud data is acquired using a navigated instrument. An FPP is identified in the intra-operative fluoroscopy images, and inputs from a navigated instrument about a location of the target surgical area are obtained. A set of landmarks relative to the identified FPP are verified using the inputs from the navigated instrument, and the location of the target surgical area is registered based on the identified FPP images and inputs from the navigated instrument, as described in patent application Ser. No. 18/743,388.

Computer-assisted navigation systems provide surgeons with computerized visualization of how a surgical instrument or other device that is posed relative to a patient correlates to a pose relative to medical images of the patient's anatomy, and how those poses correlate to a pre-operative surgical plan.

Dynamic Reference Base

Figure 17:
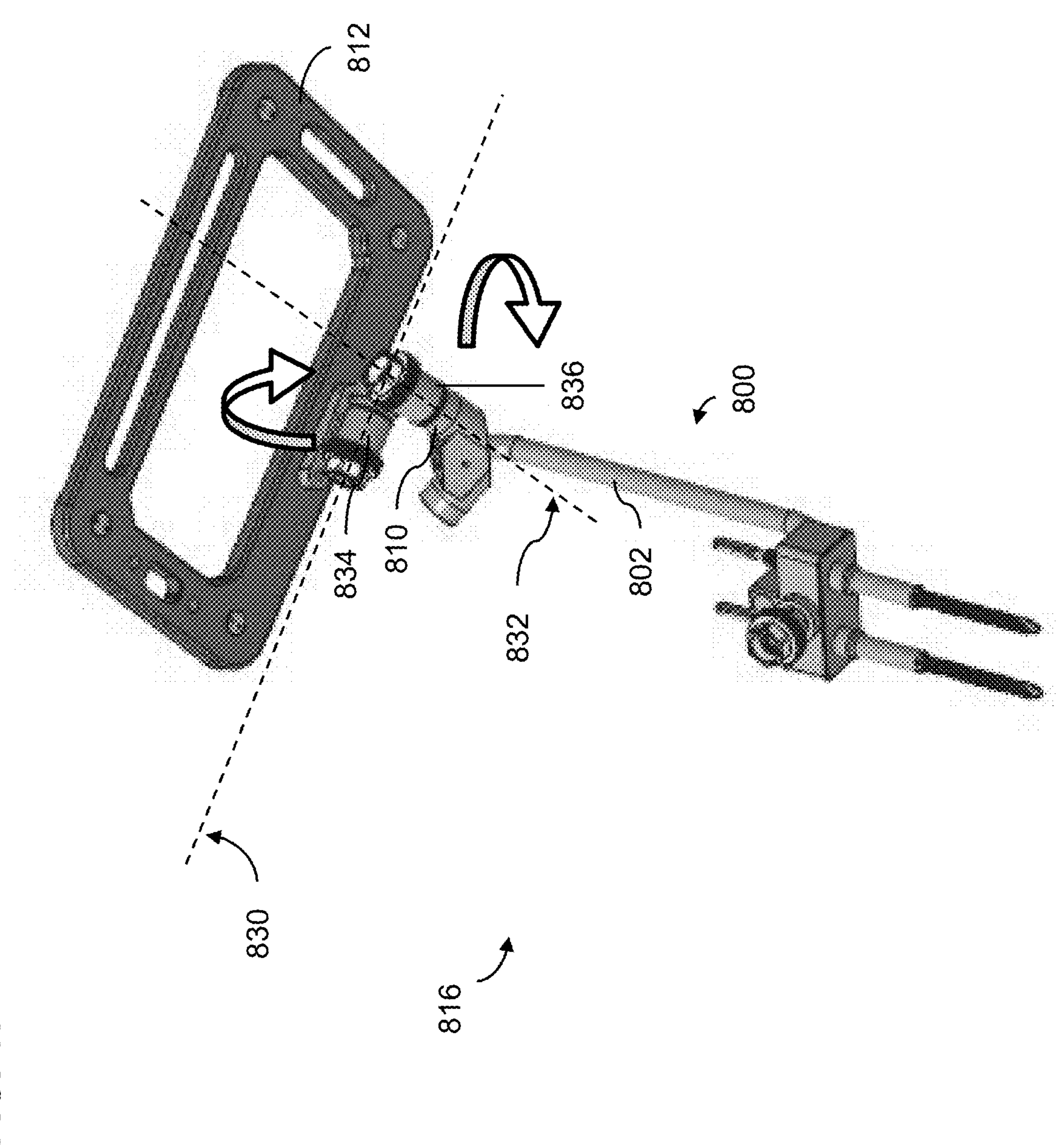
FIG. 17 provides a perspective view of the dynamic reference base in the process of adjusting the array frame, in accordance with some embodiments of the present disclosure.
Figure 18:
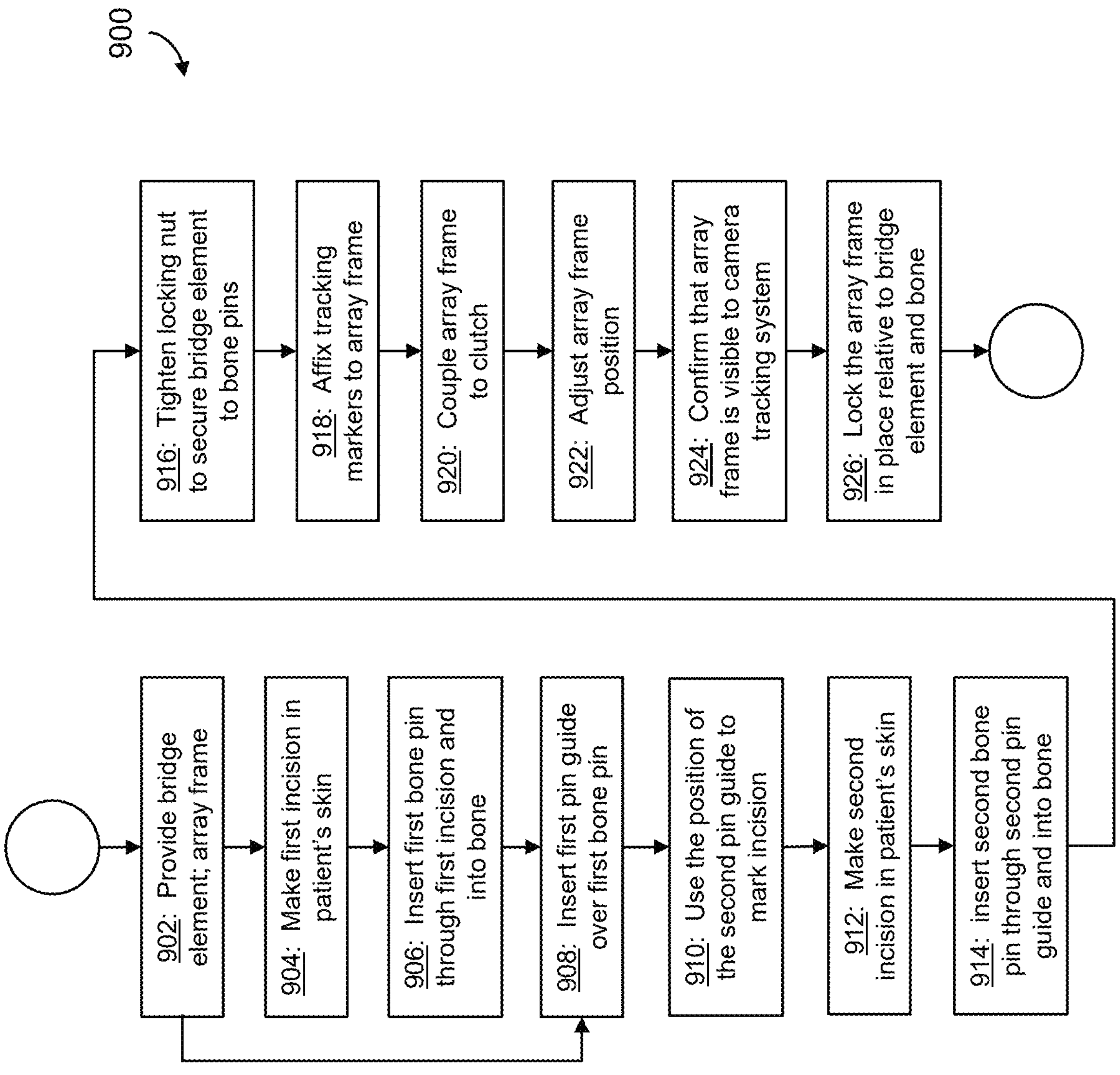
FIG. 18 provides a flow chart depicting processes in a method of affixing a dynamic reference base (DRB) to a patient, in accordance with some embodiments of the present disclosure.

As discussed herein, a dynamic reference base (DRB) or patient reference array 116 may be used to rigidly attach to patient anatomy such as bone, with stable pitch and roll relative to gravity. The DRB 116 may display an array of tracking markers in a manner that is visible to one or more tracking cameras. This may facilitate tracking of the rigid anatomy within a given measurement volume of a camera coordinate system during a navigated surgery. According to certain embodiments described here, the DRB 116 may include particular features described herein below relative to DRB 816 and depicted in FIGS. 10A-10B through FIG. 17, and FIGS. 19-20 (labeled as DRB 816, e.g., in FIGS. 13A-13B, FIGS. 16A-16B, and FIG. 17. Additionally, the flow diagram of FIG. 18 illustrates a workflow for a method of affixing a DRB such as DRB 816 to patient bone.

Figures 12A, 12B:
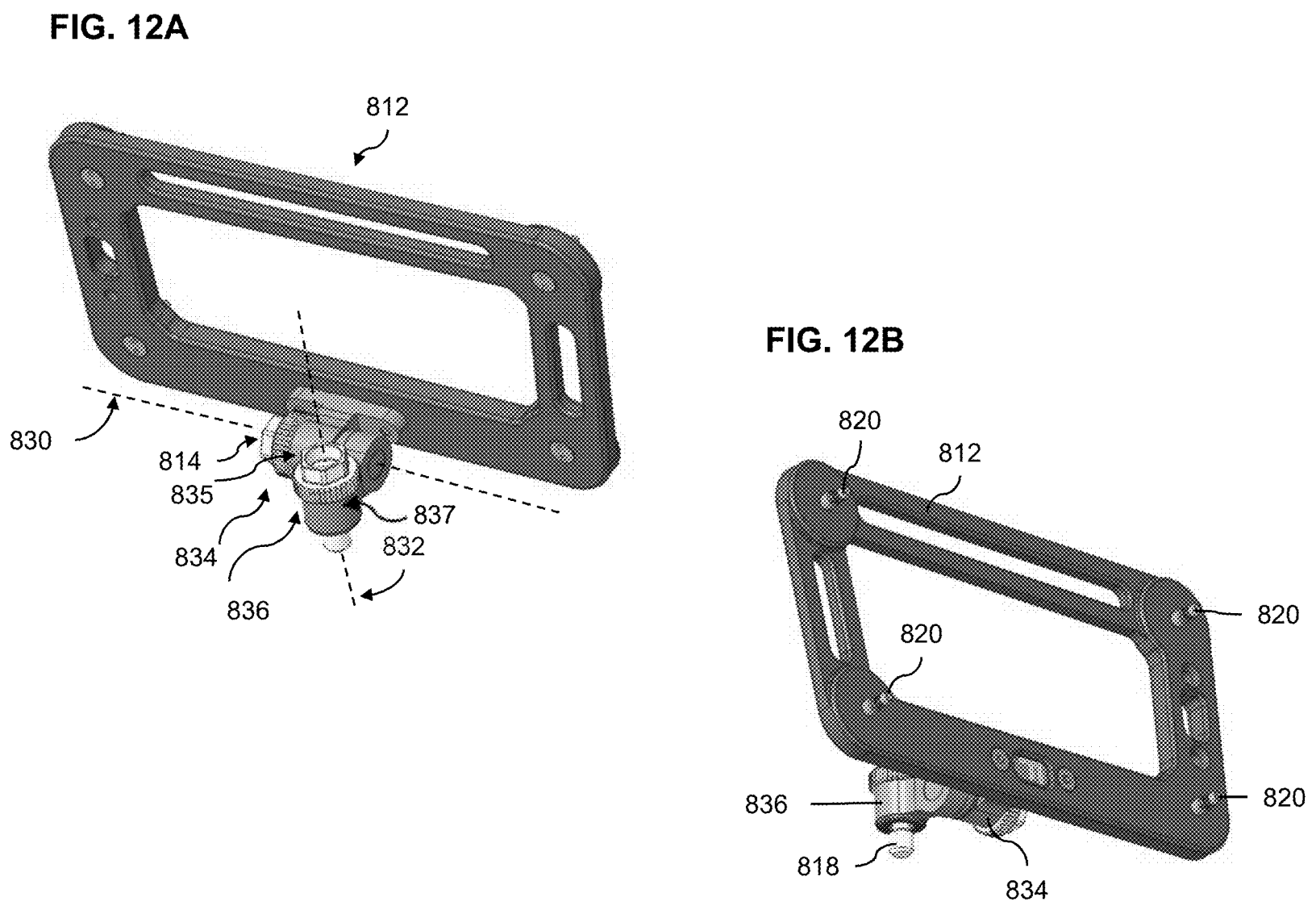
Figures 13A, 13B:
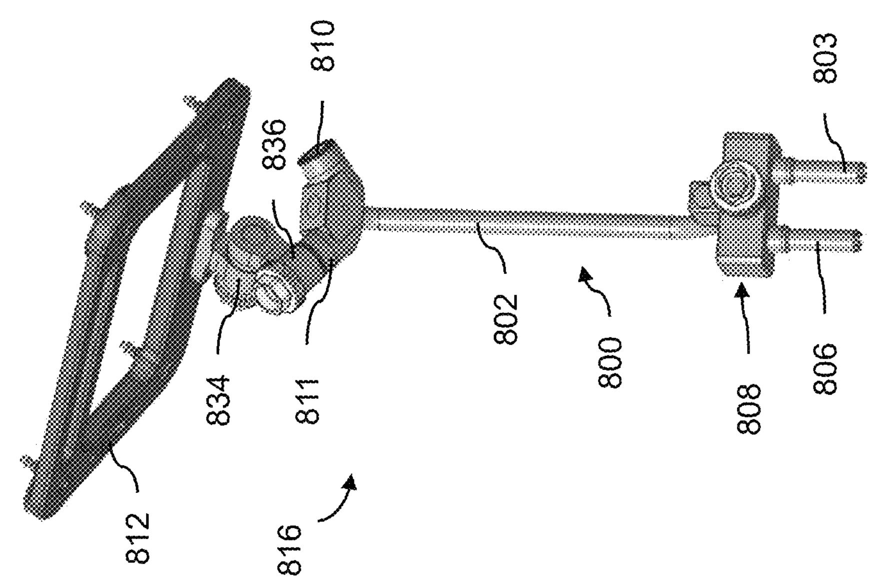
FIGS. 13A-13B provide perspective views of a dynamic reference base including the bridge element shown in FIGS. 10A-10B and the array frame shown in FIGS. 12A-12B, in accordance with some embodiments of the present disclosure.

FIGS. 13A-13B illustrate an assembled DRB 816, which may include a bridge element 800, and an array frame 812 affixed thereto. The bridge element 800 is depicted in greater detail in, e.g., FIGS. 10A-10B and 11A-11B, while the array frame 812 is depicted in greater detail in, e.g., FIGS. 12A-12B.

In various embodiments, the bridge element 800 may include a connecting rod 802 having a distal end and a proximal end. As used herein, the term "distal" refers to the direction toward attachment to the patient, and is shown as direction D in, e.g., FIG. 10A, while the term "proximal" refers to the direction away from attachment to the patient, and is shown as direction P in, e.g., FIG. 10A.

The distal end of the connecting rod 802 may be coupled to a clamp 808, which may further include first and second pin guides 803, 806 extending through and distally from the clamp 808. The first and second pin guides 803, 806 may be in the form of bores extending through the clamp 808, and tubes extending therefrom, adapted to collectively receive bone pins therein. In certain embodiments, the first and second pin guides 803, 806 may be integrated features of the bridge element 800, e.g., with the clamp 808, thereby reducing the number of components needed for placement. In any event, the first and second pin guides 803, 806 may be adapted to rigidly affix the positions of the bone pins and the bridge element 800 relative to one another. For example, the first and second pin guides 803, 806 may constrain the axial translation and rotation of bone pins about the axis of the pin disposed therein, as well constrain translation and rotation of bone pins disposed therein along and about other axes in a defined coordinate system. A locking nut 804 may be disposed on the clamp 808 and adapted to tighten the bridge element 800 to one or more bone pin(s) that may be inserted within each of the first and second pin guides 803, 806. Moreover, a ball plunger located in the clamp 808 engages with the threads of the bone pins to temporarily prevent axial translation before the clamp is fully secured with the locking nut. Also, a spring 809 in the clamp 808 keeps the clamp normally closed, that is the clamp is always engaged with the bone pins 822,824 even when there is no user interaction.

In certain embodiments, first and second bone pins 822, 824 may be disposed within each of the first and second pin guides 803, 806. Such bone pins 822, 824 may be adapted for insertion into, and rigid affixation to a patient's anatomy, e.g., the iliac crest of the patient's pelvis. In certain embodiments (scc, e.g., FIGS. 14A-14B and FIGS. 15A-15B), the bone pins 822, 824 may include external threads 828 along at least a partial axial extent thereof, and the first and second pin guides 803, 806 may include features 838 adapted to threadably engage the external threads 828.

Figure 11B:
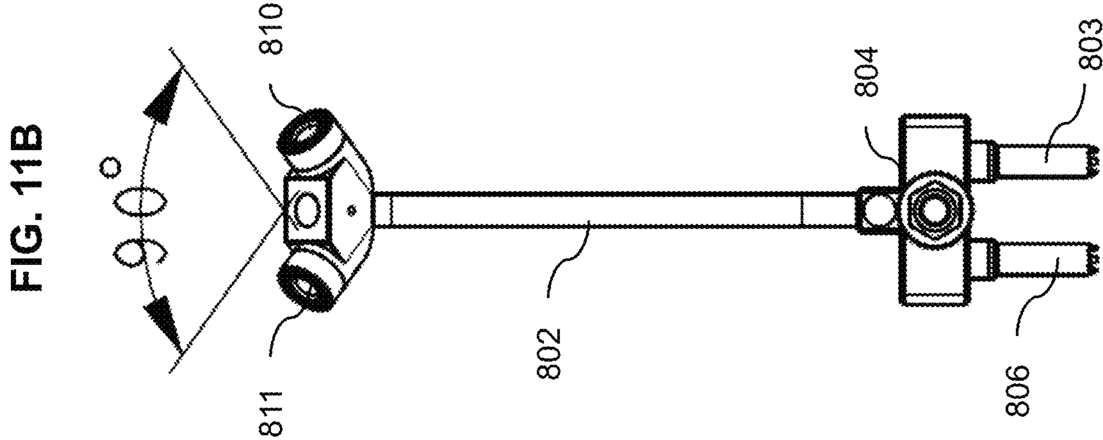
FIGS. 11A-11B provide perspective views of a bridge element of a dynamic reference base in accordance with some embodiments of the present disclosure.
Figure 11A:
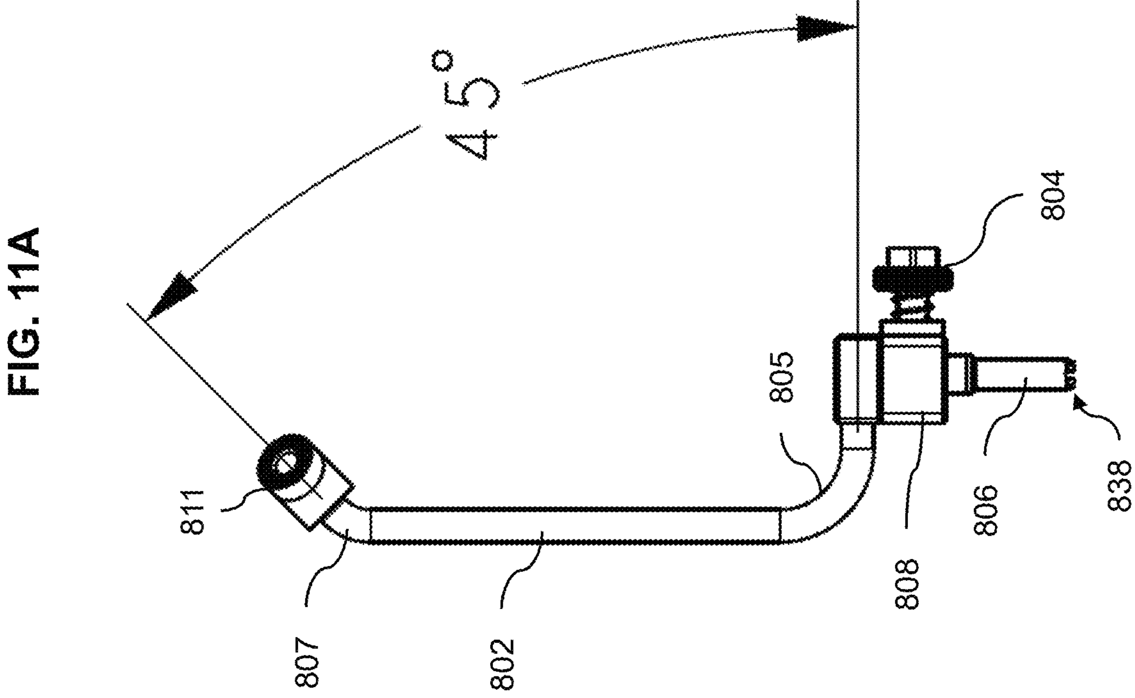

With reference to FIG. 11A, the connecting rod 802 includes an axial length that extends in a distal-proximal direction, with a first bend 805 in the rod 802 near the distal end thereof. In certain embodiments, the first bend 805 may be a bend having an angle of, e.g., approximately 90°, although other angles slightly more acute or obtuse are also contemplated. As a result, the distal end of the connecting rod 802, which is coupled to the clamp 808, and which extends beyond the bend 805, may extend perpendicularly relative to the first and second pin guides 803, 806. As discussed herein, the first and second pin guides 803, 806 extend in a distal direction from the clamp 808. Thus, from the distal end of the connecting rod 802, the connecting rod 802 extends perpendicularly relative to the direction of extension of the first and second pin guides 803, 806 until reaching bend 805. At bend 805, the connecting rod bends or curves in a proximal direction, away from the first and second pin guides 803, 806. The connecting rod 802 may extend proximally, and in some embodiments approximately parallel to the first and second pin guides 803, 806.

Continuing along the connecting rod 802 in the proximal direction, the connecting rod 802 may further include a second bend 807 near the proximal end thereof. The second bend 807 may have an angle such that the proximal end of the connecting rod 802, e.g., the portion extending proximally beyond the second bend 807, creates an angle relative to a plane created by the two bone pins 822, 824 (see, e.g., FIGS. 16A-16B). This angle may be, e.g., about 30° to about 60°. In various exemplary embodiments, the angle may be about 30°, about 35°, about 40°, about 45°, about 50°, about 55°, or about 60°. In other exemplary embodiments, the angle may be about 30° to about 35°, about 35° to about 40°, about 40° to about 45°, about 45° to about 50°, about 50° to about 55°, or about 55° to about 60°.

The proximal end of the connecting rod 802 may be coupled to a connector/clutch 810, which may be adapted to engage and affix the array frame 812. In certain embodiments, the connecting rod 802 may be coupled to a pair of connectors/clutches 810, 811, as discussed further herein. When two connectors/clutches 810, 811 are present, the first clutch 810 and the second clutch 811 may be separated by an angle which may be, e.g., about 45° to about 133° or preferably about 45° to about 90°. In the embodiment shown in FIG. 11B, an exemplary angle of about 90° is shown. However, in other embodiments, the angle may be e.g., about 45°, about 50°, about 55°, about 60°, about 65°, about 70°, about 75°, about 80°, about 85°, or about 90°. In further exemplary embodiments, the angle may be, e.g., about 45° to about 50°, about 50° to about 55°, about 55° to about 60°, about 60° to about 65°, about 65° to about 70°, about 70° to about 75°, about 75° to about 80°, about 80° to about 85°, or about 85° to about 90°. In use, as shown in, e.g., FIGS. 13A-13B, either of clutches 810 or 811 may be selected to engage a complementary fixture on the array frame 812 to couple the array frame 812 to the bridge element 800. For example, in FIG. 13A, clutch 811 is depicted engaging a complementary fixture on the array frame 812, while in FIG. 13B, clutch 810 is depicted engaging the complementary fixture on the array frame 812. As between clutch 810 and clutch 811, a user may select the preferred clutch based on, e.g., a desired position of the array frame 812, and other factors discussed further herein.

Referring back to FIGS. 12A-12B, the array frame 812 may include a first rotatable coupling 834 affixed thereto. The first rotatable coupling 834 may be adapted to rotate about a first axis 830, and to be secured in a desired rotational position relative to the first axis 830 by a locking nut 814. The array frame 812 may further include a second rotatable coupling 836 secured to the first rotatable coupling 834. The second rotatable coupling 836 may be adapted to rotate about a second axis 832. The second axis 832 is offset from first axis 830, and may in certain embodiments be perpendicular or approximately perpendicular to the first axis 830, about which the first rotatable coupling 834 may rotate. The second rotatable coupling 836 may include a captured screw 818, which may be received, e.g. threaded, into a selected one of clutch 810 or clutch 811. Similar to the spring 809, internal springs 835, 837 temporarily secure the rotational position of the coupling and allow the user to adjust before final securing with the locking nut for the first rotational coupling and captured screw for the second rotational coupling.

The array frame 812 may further include a plurality of markers disposed on the array frame 812, which may be affixed via, e.g., posts 820 (FIG. 12B). As discussed elsewhere herein, the markers may be, e.g., NIR retroreflective, NIR LED, visible, or any other type of marker adapted for use with a tracking camera and related system as described elsewhere herein.

In the bridge element 800, as a result of the angle of the clutches 810, 811 relative to the plane of the bone pins 822, 824, discussed above, the axis 832 of rotation about which the second rotatable coupling 836 rotates, may be approximately parallel to the normal of the floor in the operating room. This may be the case regardless of the bone pin insertion location on the patient. Collectively, the angular positions of the clutches 810, 811 and rotatable couplings 834, 836 are adapted to provide intuitive positioning of the array frame 812 after insertion of the captured screw 818 into the selected one of clutches 810 or 811. In one example, rotation of the second rotatable coupling 836 about second axis 832 (FIGS. 12A, 17) allows the array frame 812 to “find” or become visible to the tracking camera (e.g., tracking camera 204 of FIGS. 1-3) of the camera tracking system (e.g., camera tracking system 200 of FIG. 4), while rotation of the first rotatable coupling 834 about the first axis 830 may adjust the pitch of the array frame 812 such that the plane of the array frame aligns with the tracking camera (e.g. tracking camera 204) in a maximally visible manner.

The positions of the rotatable couplings 834, 836 near the array frame 812, i.e., at a proximal end of the bridge element 800, as opposed to, e.g., a more distal position along the connecting rod 802, offer certain advantages. For example, this arrangement enables manipulation of the array frame 812 without gross adjustment of the location, and without contacting soft tissue of the patient. Additionally, the adjustability offered by the option to use clutch 810 or clutch 811, together with the rotatability about the first and second axes 830, 832 facilitate use of the DRB 816 in a variety of patient positions on the operating table, e.g., supine, lateral, or prone, and on target surgical areas on either the left or right side of the patient.

Referring now to the illustrations in FIGS. 14A-14B through FIG. 17, and the flow chart of FIG. 18, processes in a method 900 (FIG. 18) of affixing a dynamic reference base (DRB) such as DRB 816 to a patient will now be described.

Referring to FIG. 18, at process 902, a bridge element 800 (FIGS. 10A-10B and 11A-11B) and array frame 812 (FIGS. 12A-12B) as described herein may be provided. As shown in FIG. 14A, the bridge element 800 may include a connecting rod 802 having a distal end D and a proximal end P. A clamp 808 is coupled to the distal end of the connecting rod 802; and at least one clutch 810, e.g., a pair of clutches 810, 811, is coupled to the proximal end of the connecting rod 802. The clutch(es) 810, 811 are adapted to couple to an array frame 812 as described above. A first and a second pin guide 803, 806 may extend distally from the clamp 808, and a locking nut 804 may be disposed on the clamp 808. The locking nut 804 may be adapted to selectively, e.g. by rotating the locking nut 804, constrain movement of one or more bone pins, e.g., two bone pins 822, 824, disposed within the pin guides 803, 806, relative to the bridge element 800 when the bone pins 822, 824 are positioned within the pin guides 803, 806.

In certain embodiments, at process 904 a first incision may be made in the patient’s skin. At process 906, the first bone pin 822 may be inserted through the incision created in process 904, and into rigid anatomy such as, e.g., the pelvis. In certain embodiments, the bone pins may be externally threaded.

Figures 14A, 14B:
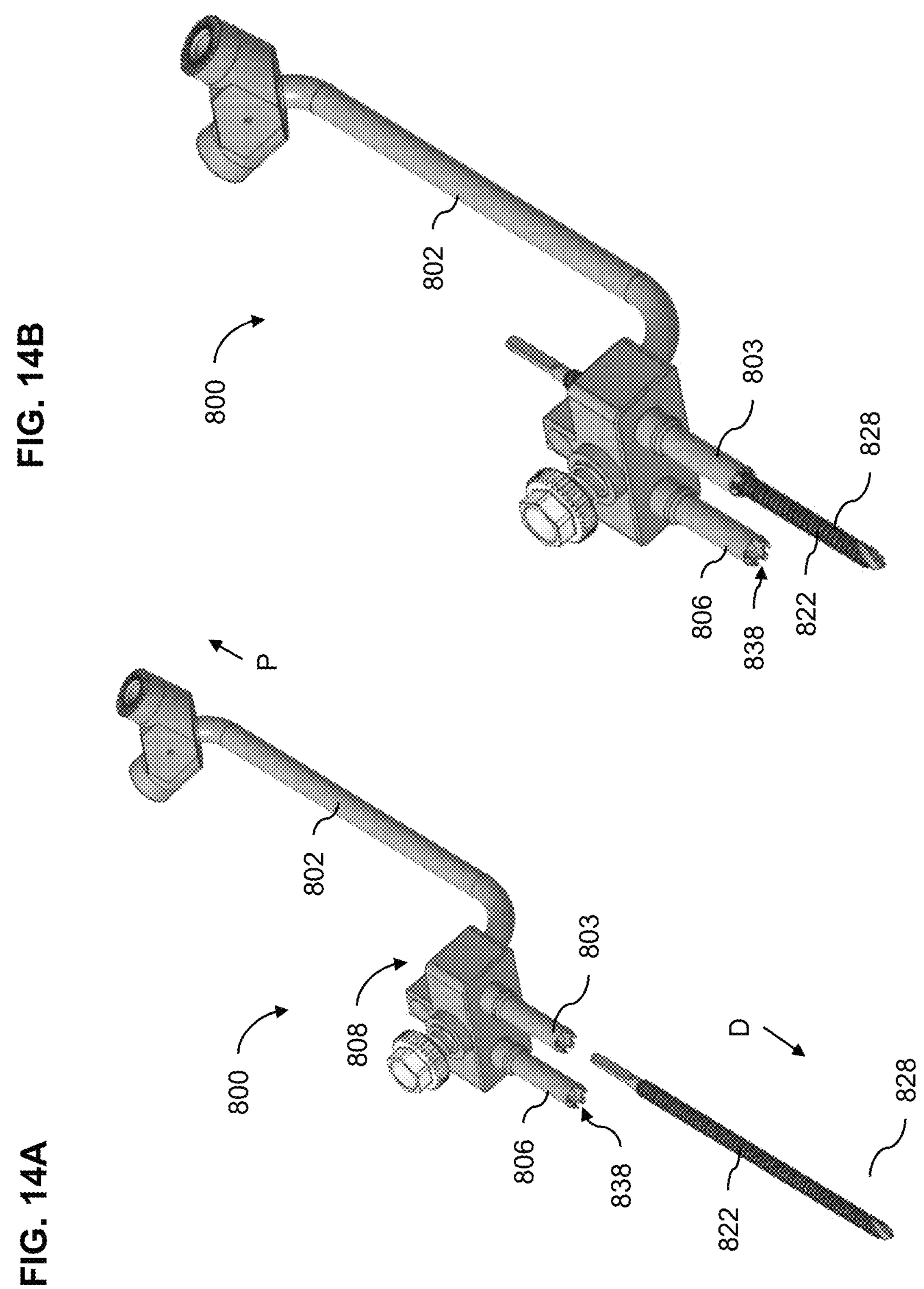
FIGS. 14A-14B provide perspective views of the bridge element shown in FIGS. 10A-10B in the process of insertion, in accordance with some embodiments of the present disclosure.

Process 908 includes inserting the first pin guide 803 over a proximal end of the first bone pin 822, as shown in FIGS. 14A-14B. The first bone pin 822 may include an external thread 828 on at least a portion of an axial extent thereof, the external thread 828 being adapted to mate with and engage a corresponding feature 838 in the first pin guide 803. In such embodiments, inserting the first pin guide 803 over the first bone pin 822 may include threading the first pin guide 803 of the bridge element 800 over the proximal end of the first bone pin 822.

Figure 15B:
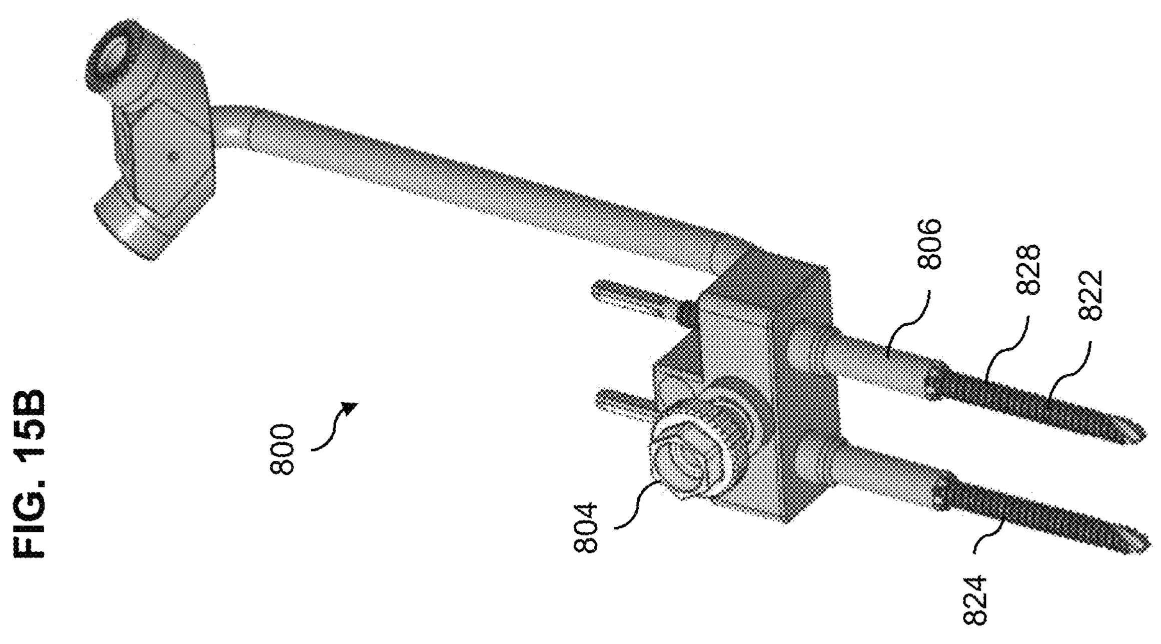
FIGS. 15A-15B provide perspective views of the bridge element shown in FIGS. 10A-10B and bone pins in the process of insertion, in accordance with some embodiments of the present disclosure.
Figure 15A:
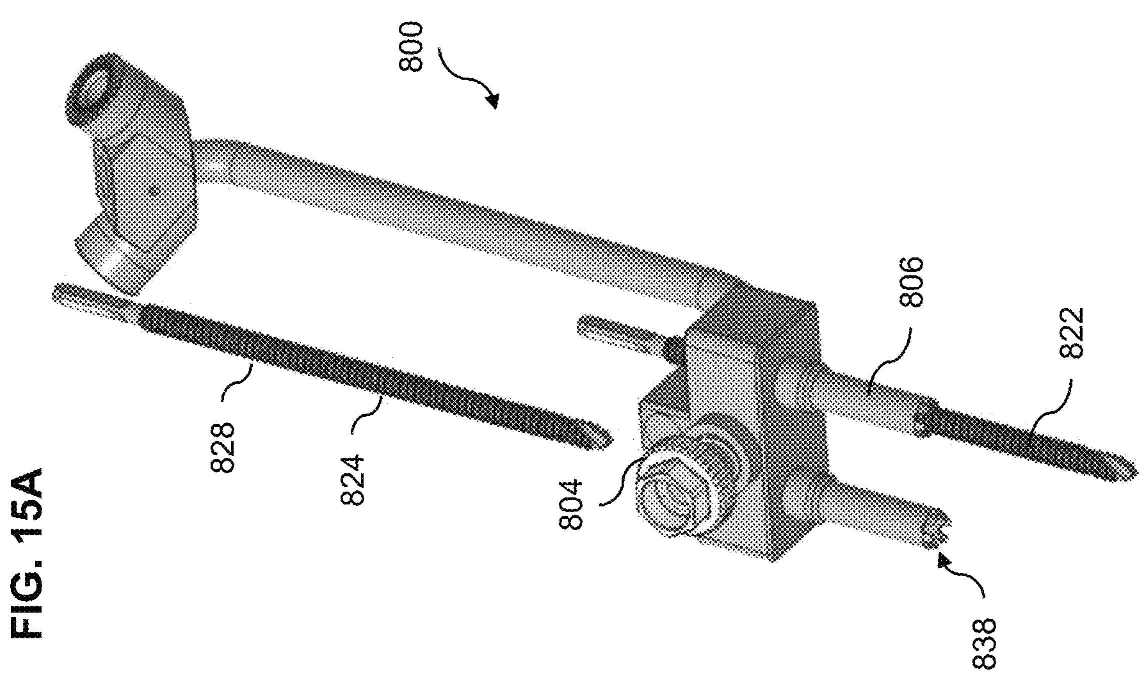

Process 910 includes using the position of the second pin guide 806 to mark a location for a second incision in the patient’s skin. Process 912 includes making the second incision in the patient’s skin at the location marked in process 910. Process 914 includes inserting the second bone pin 824 through the second pin guide 806, as shown in FIGS. 15A-15B, and into the second incision. The inserting may further include inserting the second bone pin 824 into rigid anatomy of the patient, as described herein relative to the first bone pin 822 and shown in FIGS. 19-20.

In certain embodiments, the second bone pin 824 may include an external thread 828 on at least a portion of an axial extent thereof, the external thread 828 being adapted to mate with and engage a feature 838 of the second pin guide 806. In such embodiments, inserting the second bone pin 824 into the second pin guide 806 may include threading a distal end of the second bone pin 824 into a proximal end of the second pin guide 806, and threading the second bone pin 824 distally through the second pin guide 806.

Figure 19:
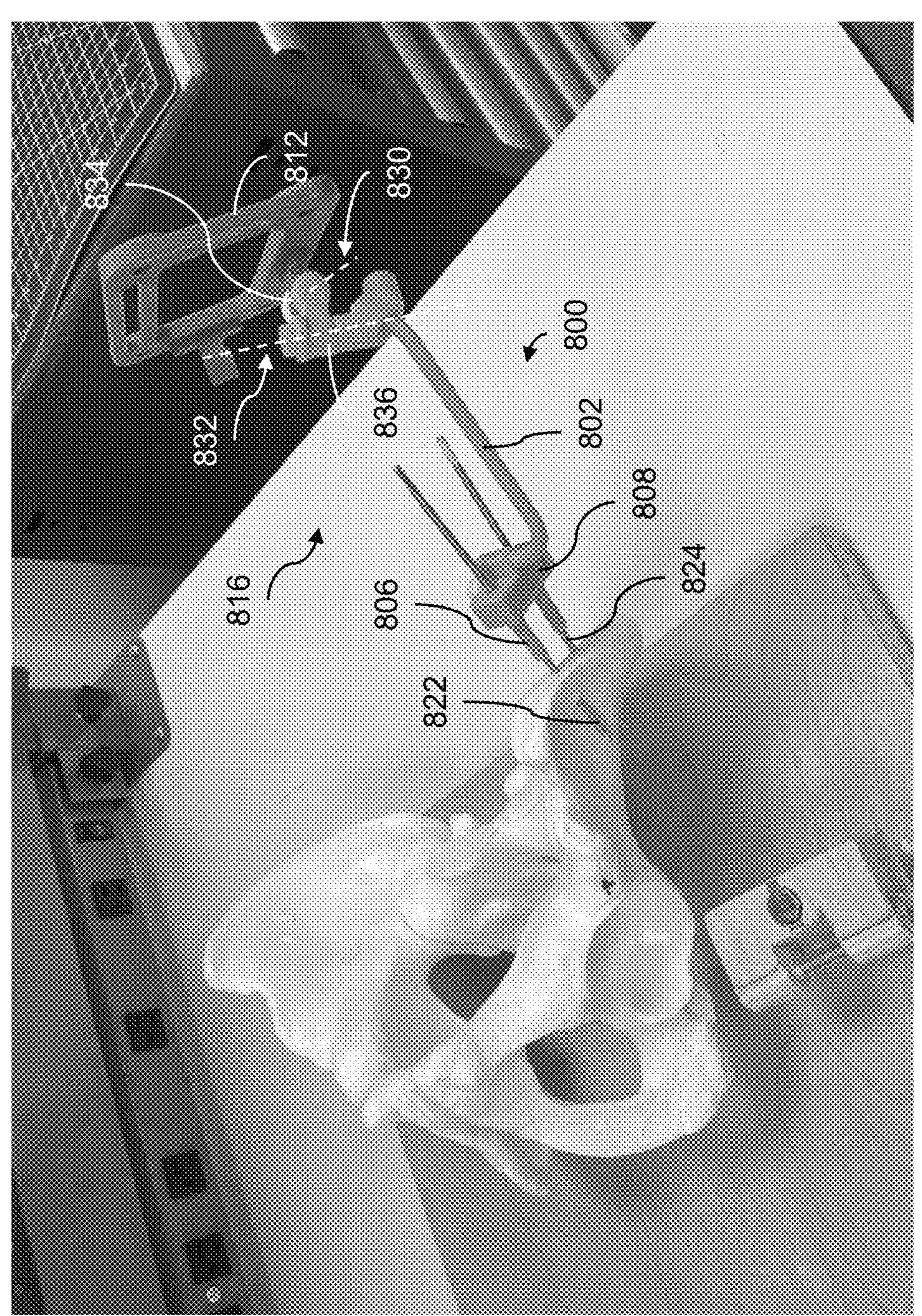
FIG. 19 provides a perspective view of the dynamic reference base affixed to the iliac crest of a pelvis, in accordance with some embodiments of the present disclosure.
Figure 20:
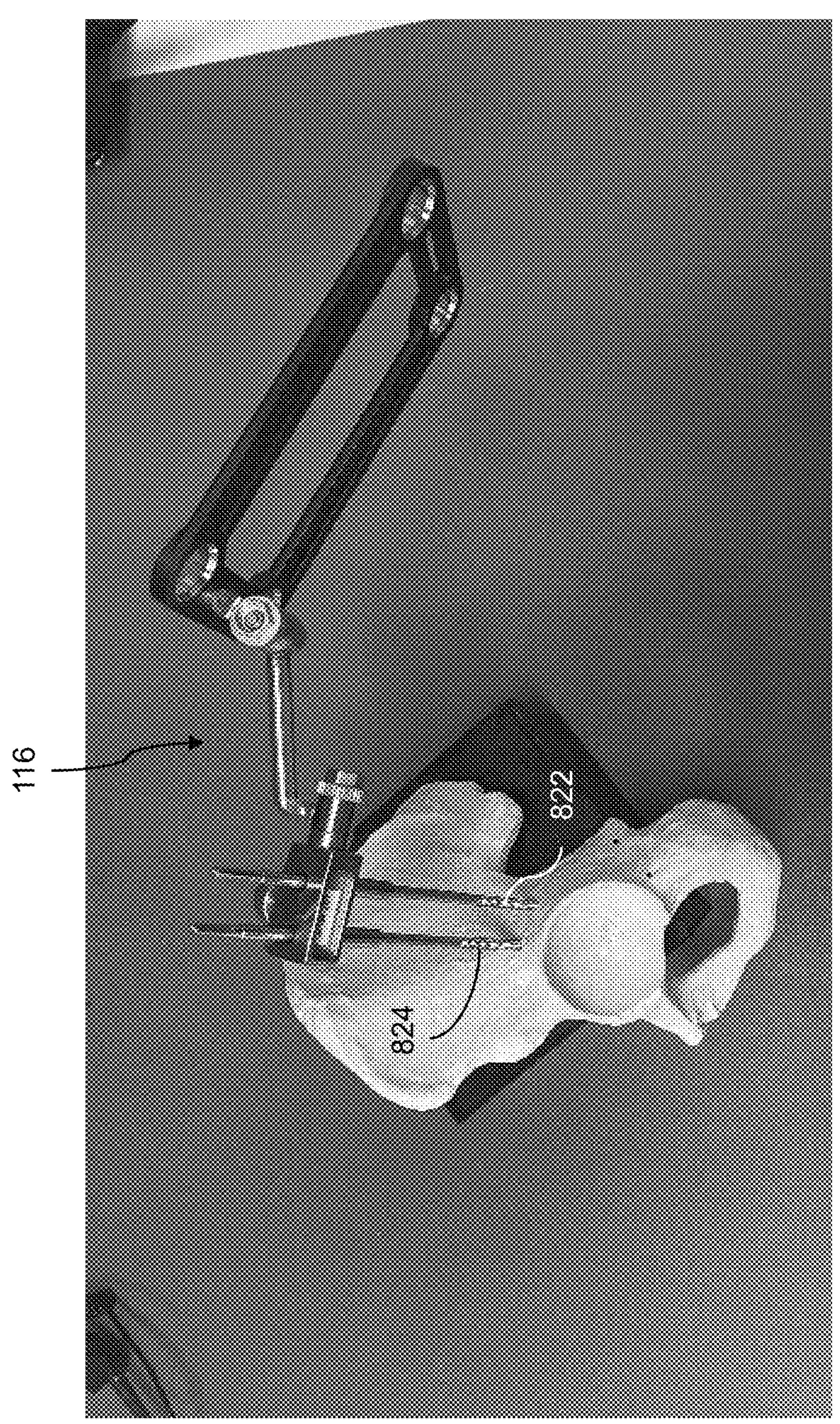
FIG. 20 provides a perspective view of a dynamic reference base affixed to a pelvis at a location superior to the rim of the acetabulum, in accordance with some embodiments of the present disclosure.

When the first and second bone pins 822, 824 are in the desired locations, process 916 includes tightening the locking nut 204, e.g., by rotating the locking nut in a direction selected from clockwise or counterclockwise, depending on the thread pattern thereof, in order to secure the bridge element 800 to the first and the second bone pins 822, 824. Locking the bone pins 822, 824 to the bridge element 800 provides rigid affixation of the eventual DRB 816 to the patient’s anatomy. In one exemplary placement, FIG. 19 illustrates the DRB 816 rigidly affixed by first and second bone pins 822, 824 into the iliac crest. In another exemplary placement, FIG. 20 illustrates first and second bone pins 822, 824 inserted in a position superior to the rim of the acetabulum at the 12 o’clock position to affix a DRB 116. Other pin placements, in the pelvis and in other rigid anatomy, may be equally suitable to rigidly affix a DRB such as DRB 816 for use in navigated or robotic surgery procedures as described herein.

Referring back to FIG. 18, process 918 includes attaching tracking markers to the array frame 812. In various embodiments, the tracking markers may be affixed to the array frame 812 by posts 820 (FIG. 12B), and may include, e.g., NIR retroreflective, NIR LED, visible, or any other type of marker adapted for use with a tracking camera and related systems as described herein.

Figures 16A, 16B:
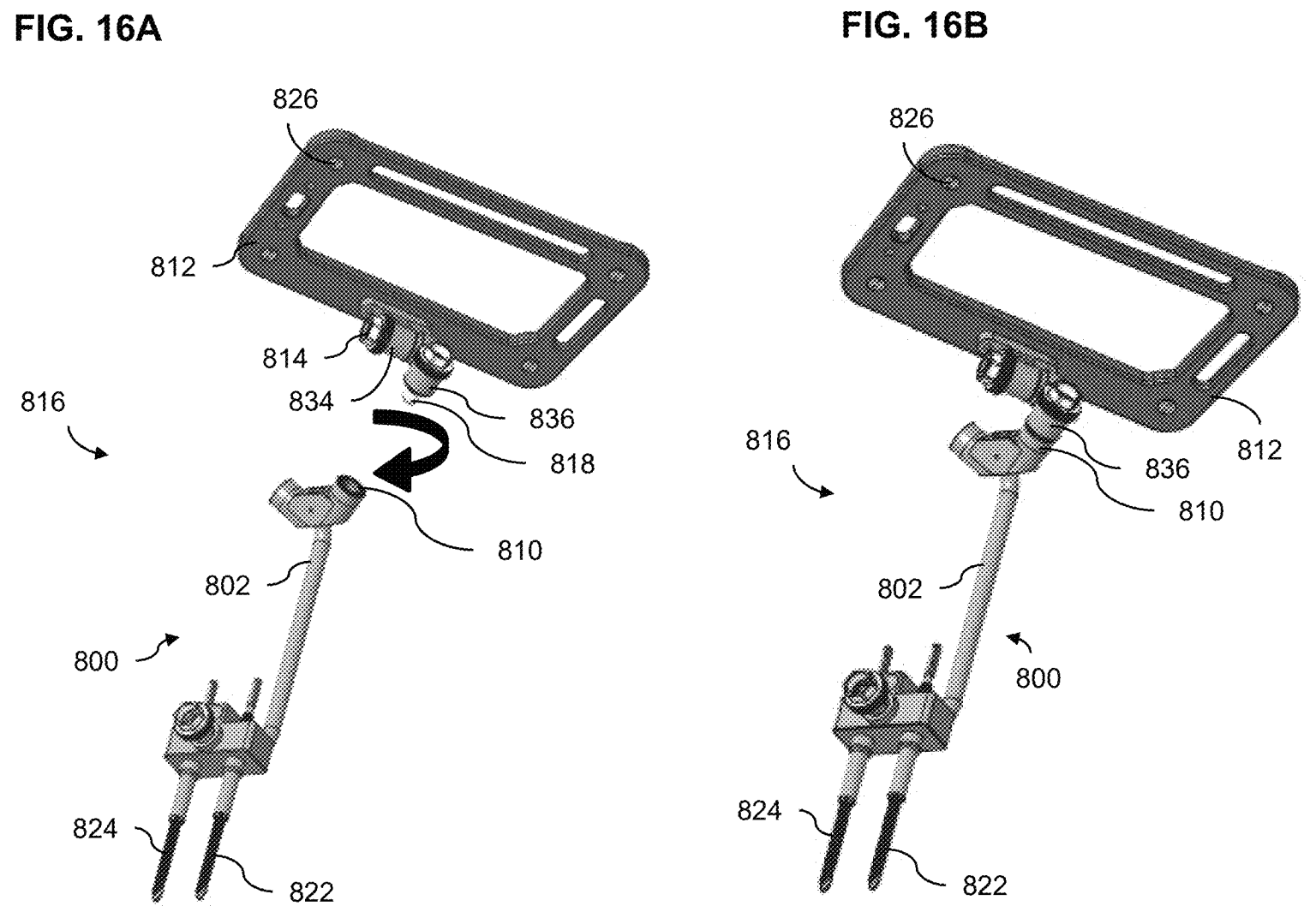

Process 920 includes coupling the array frame 812 to the clutch 810 (or clutch 811), as shown in FIGS. 16A-16B. As described above, the array frame 812 may include a first rotatable coupling 834 affixed thereto. The first rotatable coupling may be adapted to rotate about a first axis 830 (FIG. 17), and to be secured in a rotational position relative to the first axis 830 by a locking nut 814 (shown in FIG. 12A). The array frame 812 may further include a second rotatable coupling 836 secured to the first rotatable coupling 834. The second rotatable coupling 834 may be adapted to rotate about a second axis 832. First and second axes 830, 832 may be offset from one another, e.g., axes 830 and 832 may be perpendicular or approaching perpendicular to one another. The second rotatable coupling 836 may include a captured screw 818. In process 920, coupling the array frame 812 to the clutch 810 may include, e.g., at least partially threading the captured screw 818 of the array frame 812 onto the selected clutch 810 (or 811) of the bridge element 800 (FIG. 16A). The user, e.g., surgeon 120 (FIG. 1), may select either clutch 810 or clutch 811 for affixation of the array frame 812 based on a number of factors such as, e.g., a position of the patient on the operating table (e.g., supine, lateral, or prone), whether the DRB 816 is affixed to anatomy on the patient's right or left side, and the location of a tracking camera to which visibility of the array frame is desired.

Process 922 includes adjusting a position of the array frame 812. Such adjustment may be relative to, e.g., one or more axes in a defined coordinate system (e.g., camera coordinate system, navigation coordinate system, etc.). As shown in FIG. 17, this may include rotating the second rotatable coupling 836, including the captured screw 818, about the second axis 832, thereby allowing the array frame 812 to "find" or become visible to the tracking camera (e.g., tracking camera 204 of FIGS. 1-3). The adjusting of process 922 may further include rotating the first rotatable coupling 834 about the first axis 830 to adjust the pitch of the array frame 812 such that the plane of the array frame 812 aligns with the tracking camera (e.g. tracking camera 204) in a maximally visible manner.

Process 924 includes, after adjusting the position of the array frame 812 in process 922, confirming that the array frame 812 is visible to a tracking camera. This may include, e.g., visual confirmation, or other means of confirming.

Process 926 includes locking the array frame 812 into place relative to the bridge element 800. This may include tightening the captured screw 818 and the locking nut 814 to lock rotation of the rotatable couplings 836 and 834, respectively, thereby locking the array frame 812 into place relative to the bridge element 800.

In various embodiments, certain of the foregoing steps may be performed in an order that differs from that presented above and depicted in FIG. 18. For example, process 918, in which markers are attached to the array frame 812, may be performed between processes 916 and 920 as shown, or it may be performed later in the workflow 900, e.g., after the array frame 812 is coupled to a clutch 810 or 811, or after the array frame 812 is rigidly fixed in position. In other embodiments, certain processes may be performed more than once, e.g., the adjustments of process 922 and confirmation of process 924 may collectively be performed iteratively as needed before moving on to locking the array frame in place in process 926, as needed to achieve the desired alignment and positioning. Other embodiments, orders, and combinations of steps are also possible within the scope and spirit of the disclosure. The flow diagram of FIG. 18 merely presents one possible arrangement or process flow.

Further Definitions and Embodiments

In the above description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected," "coupled," "responsive," or variants thereof to another element, it can be directly connected, coupled, or responsive to the other element or intervening elements may be present. In contrast, when an element is referred to as being "directly connected," "directly coupled," "directly responsive," or variants thereof to another element, there are no intervening elements present. Like numbers refer to like elements throughout. Furthermore, "coupled," "connected," "responsive," or variants thereof as used herein may include wirelessly coupled, connected, or responsive. As used herein, the singular forms "a," "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise," "comprising," "comprises," "include," "including," "includes," "have," "has," "having," or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.," which derives from the Latin phrase "exempli gratia," may be used to introduce or specify a general example or examples of a previously mentioned item, and is not intended to be limiting of such item. The common abbreviation "i.e.," which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A dynamic reference base (DRB) comprising:
- a bridge element including:
  - a connecting rod having a distal end and a proximal end;
  - a clamp coupled to the distal end of the connecting rod;
  - a first clutch coupled to the proximal end of the connecting rod, the first clutch being adapted to couple to an array frame;
  - a first and a second pin guide extending distally from the clamp; and
  - a locking nut disposed on the clamp and adapted to tighten the bridge element to a bone pin disposed within each of the first and second pin guides; and
- the array frame affixed to the first clutch,
- wherein the first clutch includes a first rotatable coupling and a second rotatable coupling, the first rotatable coupling having an axis of rotation that is generally perpendicular to an axis of rotation of the second rotatable coupling.

2. The DRB of claim 1, wherein the bridge element further comprises a second clutch.

3. The DRB of claim 2, wherein the first clutch and the second clutch are separated by an angle of about 45° to about 135°.

4. The DRB of claim 1, wherein the connecting rod further includes:
- a first portion located at the distal end thereof, extending perpendicularly relative to the first and second pin guides, and
- a first bend, transitioning from the first portion to a second portion extending proximally, away from a direction of the first and second pin guides.

5. The DRB of claim 4, wherein the connecting rod further includes: a second bend between the second portion and a third, proximal-most portion, wherein the third, proximal-most portion extends at an angle of about 30 to about 60 degrees relative to a plane defined by the first and second pin guides.

6. The DRB of claim 1, wherein the first and second pin guides are integrated with the clamp.

7. The DRB of claim 1, wherein:
- the first rotatable coupling is secured in rotational position by a locking nut; and
- the second rotatable coupling is secured to the first rotatable coupling, the second rotatable coupling including a captured screw adapted to be received in the first clutch.

8. The DRB of claim 1, further comprising a plurality of markers disposed on the array frame.

9. The DRB of claim 1, further comprising a bone pin disposed in each of the first and second pin guides.

10. The DRB of claim 9, wherein each bone pin is adapted for insertion into a pelvis of a patient.

11. A method of affixing a dynamic reference base (DRB) to a patient, comprising:
- providing an array frame and a bridge element including:
  - a connecting rod having a distal end and a proximal end;
  - a clamp coupled to the distal end of the connecting rod;
  - a clutch coupled to the proximal end of the connecting rod, the clutch being adapted to couple to the array frame;
  - a first and a second pin guide extending distally from the clamp; and
  - a locking nut disposed on the clamp;
- making a first incision in the patient's skin;
- inserting the first bone pin through the first incision into a pelvis of the patient;
- inserting the first pin guide over the first bone pin;
- using the position of the second pin guide to mark a location for a second incision;
- making the second incision on the patient's skin;
- inserting the second bone pin through the second pin guide;
- tightening the locking nut to secure the bridge element to the first and the second bone pins;
- coupling the array frame to the clutch;
- adjusting a position of the array frame relative to a first axis and a second axis in a defined coordinate system; and
- locking the array frame into place relative to the bridge element.

12. The method of claim 11, further comprising:
- attaching tracking markers to the array frame.

13. The method of claim 11, wherein inserting the second bone pin further comprises inserting the second bone pin into an iliac crest of the patient.

14. The method of claim 11, wherein the array frame comprises:

a first rotatable coupling secured thereto and rotatable about a first axis, and securable in rotational position by a locking nut; and a second rotatable coupling secured to the first rotatable coupling and rotatable about a second axis, the second rotatable coupling including a captured screw adapted to be received in the clutch, and wherein coupling the array frame to the clutch comprises at least partially threading the captured screw into the clutch of the bridge element.

15. The method of claim 14, wherein adjusting the position of the array frame further comprises:

rotating the second rotatable coupling about the second axis; and rotating the first rotatable coupling about the first axis, wherein the first axis and the second axis are approximately perpendicular to one another.

16. The method of claim 15, wherein locking the array frame into position relative to the bridge element further comprises:

tightening the captured screw of the second rotatable coupling and the locking nut of the first rotatable coupling.

17. The method of claim 11, further comprising:

after adjusting the position of the array frame, confirming that the array frame is visible to a tracking camera.

18. The method of claim 11, wherein the clutch of the bridge element is one of a pair of clutches coupled to the proximal end of the connecting rod, each clutch of the pair of clutches being adapted to couple to the array frame, and wherein the pair of clutches are separated from one another by an angle of about 45° to about 135°, and wherein the coupling of the array frame to the clutch further comprises selecting one clutch from the pair of clutches, based in part on one or more of:

whether the dynamic reference base is affixed to a left or a right side of the patient, a location of a tracking camera to which visibility of the array frame is desired, or a position of the patient on an operating table.

* * * * *